United States Patent
Marcus

(10) Patent No.: US 6,750,449 B2
(45) Date of Patent: Jun. 15, 2004

(54) SAMPLING AND ANALYSIS OF AIRBORNE PARTICULATE MATTER BY GLOW DISCHARGE ATOMIC EMISSION AND MASS SPECTROMETRIES

(75) Inventor: R. Kenneth Marcus, Clemson, SC (US)

(73) Assignee: Clemson University, Clemson, SC (US)

( * ) Notice: Subject to any disclaimer, the term of this patent is extended or adjusted under 35 U.S.C. 154(b) by 511 days.

(21) Appl. No.: 09/934,273

(22) Filed: Aug. 21, 2001

(65) Prior Publication Data
US 2002/0003210 A1 Jan. 10, 2002

Related U.S. Application Data

(63) Continuation of application No. PCT/US00/04793, filed on Feb. 25, 2000.
(60) Provisional application No. 60/121,559, filed on Feb. 25, 1999.

(51) Int. Cl.[7] .................................................. H01J 49/04
(52) U.S. Cl. .................. 250/288; 250/281; 250/287
(58) Field of Search ................................ 250/288, 281, 250/287, 282, 285, 423 R

(56) References Cited

U.S. PATENT DOCUMENTS

| | | |
|---|---|---|
| 4,167,667 A | 9/1979 | Hall et al. |
| 4,368,850 A | 1/1983 | Szekely |
| 4,381,664 A | 5/1983 | Clark et al. |
| 4,383,171 A | 5/1983 | Sinha et al. |
| 4,687,929 A | 8/1987 | Browner et al. |
| 4,762,995 A | 8/1988 | Browner et al. |
| 4,808,827 A | 2/1989 | Woollam |
| 4,872,786 A | 10/1989 | Braden |
| 4,883,958 A | 11/1989 | Vestal |
| 4,924,097 A | 5/1990 | Browner et al. |
| 4,928,537 A | 5/1990 | Liu et al. |
| 5,006,706 A | 4/1991 | Marcus |
| 5,086,226 A | 2/1992 | Marcus |
| 5,096,615 A | 3/1992 | Prescott et al. |
| 5,175,433 A | 12/1992 | Browner et al. |
| 5,184,016 A * | 2/1993 | Ronan et al. ............... 250/288 |
| 5,192,865 A * | 3/1993 | Zhu ........................... 250/288 |
| 5,266,192 A * | 11/1993 | Ligon et al. ............. 210/198.2 |
| 5,319,575 A | 6/1994 | Lilienfeld |
| 5,325,021 A | 6/1994 | Duckworth et al. |
| 5,331,160 A | 7/1994 | Whitt |
| 5,345,079 A | 9/1994 | French et al. |
| 5,382,794 A * | 1/1995 | Downey et al. ............ 250/288 |
| 5,400,665 A | 3/1995 | Zhu et al. |
| 5,408,315 A | 4/1995 | Mitchell et al. |

(List continued on next page.)

OTHER PUBLICATIONS

Book of Abstracts, Pittcon® '98, Mar. 1–5, 1998.
Celia Henry, Dust in the Wind, Analytical Chemistry News & Features, Jul. 1, 1998.
Technical Information, Model PT1000/CY2000 Particle Analyzer System, Yokogawa Electric Corporation, Mar. 1996.

(List continued on next page.)

Primary Examiner—John R. Lee
Assistant Examiner—Johnnie L. Smith, II
(74) Attorney, Agent, or Firm—Dority & Manning, P.A.

(57) ABSTRACT

The apparatus and methods employ momentum separation to implement a particle beam (PB) sampling scheme for the introduction of particulate matter into low pressure (e.g., glow discharge) plasma sources for subsequent atomic emission and mass spectrometry chemical analysis in real time, whether the particles are provided in a continuous stream during the analysis or are collected in situ and analyzed periodically upon obtaining a suitable number of particles to be analyzed. The particulate matter in the particle beam (PB) is subjected to low-power laser scattering to effect particle size analysis. Gases removed by momentum separation are also analyzed.

24 Claims, 25 Drawing Sheets

U.S. PATENT DOCUMENTS

| | | | |
|---|---|---|---|
| 5,410,918 A | | 5/1995 | Zimmerman |
| 5,412,975 A | | 5/1995 | Raabe et al. |
| 5,437,198 A | | 8/1995 | John |
| 5,500,369 A | | 3/1996 | Kiplinger |
| 5,565,677 A | | 10/1996 | Wexler et al. |
| 5,681,752 A | | 10/1997 | Prather |
| 5,896,196 A | * | 4/1999 | Pinnaduwage ............. 356/311 |
| 5,998,215 A | * | 12/1999 | Prather et al. ............. 436/173 |
| 6,040,574 A | * | 3/2000 | Jayne et al. ................. 250/288 |
| 6,465,776 B1 | * | 10/2002 | Moini et al. ................. 250/285 |
| 6,566,652 B1 | * | 5/2003 | Kato ........................... 250/288 |

OTHER PUBLICATIONS

Jianzhang You, Melissa A. Dempster, and R. Kenneth Marcus, Analysis of Organic Compounds by Particle Beam/Hollow Cathode Atomic Emission Spectroscopy: Determinations of Carbon and Hydrogen in Amino Acids, Analytical Chemistry, vol. 69, No. 17, Sep. 1, 1997.

Jianzhang You, Patrick A. DePalma, Jr., and R. Kenneth Marcus, Nebulization and Anaysis Characteristics of a Particle Beam–Hollow Cathode Glow Discharge Atomic Emission Spectrometry System, Journal Of Analytical Atomic Spectrometry, Jul. 1996, vol. 11 (483–490).

Cynthia M. Strange and R. Kenneth Marcus, Aqueous Sample Introduction into a Glow Discharge Device Via a Particle Beam Interface, Spectrochimica Acta. vol. 46B, No. 4, pp. 517–426, 1991.

Jianzhang You, Melissa A. Dempster and R. Kenneth Marcus, Studies of Analyte Particle Transport in a Particle Beam–Hollow Cathode Atomic Emission Spectrometry System, Journal of Analytical Atomic Spectrometry, Aug. 1997, vol. 12 (807–815).

Jianzhang You, James C. Fanning, and R. Kenneth Marcus, Particle Beam Aqueous Sample Introduction for Hollow Cathode Atomic Emission Spectroscopy, Analytical Chemistry, vol. 66, No. 22, Nov. 15, 1994.

Sylvia H. Wood, Kimberly A. Prather, Time–of–Flight Mass Spectrometry Methods for Real Time Analysis of Individual Aerosol Particles, Trends in Analytical Chemistry, vol. 17, No. 6, 1998.

* cited by examiner

SAMPLING AND ANALYSIS OF AIRBORNE PARTICULATE MATTER BY GLOW DISCHARGE ATOMIC EMISSION AND MASS SPECTROMETRIES

CROSS-REFERENCE TO RELATED APPLICATIONS

This application claims priority to U.S. Provisional Application Ser. No. 60/121,559 filed Feb. 25, 1999, and is a Continuation of PCT International Application Serial No. PCT/US00/04793 filed Feb. 25, 2000.

BACKGROUND OF THE INVENTION

The present invention relates to apparatus and methods for analyzing and characterizing airborne particulate matter and more particularly to such apparatus and methods operating in real time.

This invention was developed with the use of funding provided in part by the combination of funding from Westinghouse Savannah River Technology Center pursuant to contract no. 3-30-1905-xxxx-32-4716 and the National Science Foundation pursuant to grant DMR-9727667.

The development of analytical methods for the characterization of airborne particulate matter has become an area of increasing activity over the last 15 years. The driving forces for these investigations lie across many fields of application, including environmental health and safety, atmospheric sciences, clean room quality control, and battlefield/non-proliferation monitoring.

Perhaps the greatest impetus for the development of new apparatus and methods of particle characterization has been the evolution of new air quality standards currently underway in the United States. Specifically, the U.S. Environmental Protection Agency (EPA) has proposed the PM2.5 standard for airborne particulate matter (hereafter "the PM2.5 standard"). The PM2.5 standard limits the density of particles of less than 2.5 micrometers in diameter to a value of 15 $\mu g/m^3$ on an annual basis. The PM2.5 standard does not include any parameters that refer to the chemical composition of airborne particles, only their size distribution/density (2).[1] The majority of the fields of application mentioned above rely on both particle classification based on size distribution as well as chemical composition (i.e., higher levels of information are required). As the pathogenic effects of particle composition become more apparent (which may in fact be driven through the development of improved analytical methods), it is easy to envision that more comprehensive regulations will evolve.

[1] The numbers within the parentheses refer to the numbered endnotes at the end of the application.

The characterization of airborne particulate matter is usually classified according to the sample system from which the chemical information is desired; batch or single particle. Given the wide range of possible sample types and information requirements, it is clear that no single method will be applicable in all cases. In fact, the classification of batch or single particle fields of application are an effective way to address capabilities.

In a batch sample system, particle size distributions and gross composition information are usually the intended goals. This type of analysis is most often applied in process monitoring situations where particle size distribution is often the most relevant piece of information.

In the case of single particle analysis, particle size and composition (elemental or molecular) are determined in order to assess the "chemistry" of a given system. These evaluations seek to define size/composition relationships, determine the distribution of species within/on a single or individual particle, and study chemical reactions at a particle's surface. Beyond providing basic size/composition information, the requirements placed upon analytical instruments used in particle characterization include aspects of sample size, sample preparation/processing, analytical time frame, portability/remote monitoring capabilities, and instrument cost and complexity.

The most significant advances over the last decade in the analysis of airborne particulate matter have occurred in the area of single particle analysis (3-16). Some of these analytical methods involve collection of particles on inert filter supports for subsequent analysis by microbeam techniques. Others involve direct, real time sampling/analysis of individual particles by instruments which may be taken out into the field.

Van Grieken et al. Analyst, volume 120, pages 681–692 (1995) have reviewed the application of charged particle microbeam methods (e.g., EPMA, PIXE, SIMS) for the characterization of individual, collected particles. While these methods are quite powerful, particularly when used in tandem, the acts of particle collection, transport, and analyses in high vacuum environments present a number of drawbacks including poor temporal resolution, questions of representation, and possible loss of volatile analytes.

Real time single particle analysis methods often involve laser-induced vaporization/excitation/ionization and atomic emission or mass spectrometric detection. In the realm of elemental analysis, laser induced breakdown spectroscopy (LIBS) (4, 5) and laser excited atomic fluorescence (LEAF) (6) following thermal dissociation provide individual particle information. Hahn (5) used the 1064 nm fundamental output of a Nd:YAG laser to vaporize desolvated particles produced with a conventional solution nebulizer. Use of 1 $\mu m$ diameter Fe-doped polymer beads permitted the establishment of emission intensity/particle size relationships. Implicit in any quantification scheme of this sort is the summation of the responses of all species present in each particle. This of course requires a priori knowledge of the sample composition.

Panne and co-workers (6) diverted one-half of the flow from a nebulizer/desolvation system through a differential mobility particle sizer (DMPS) and the other half through the path of a vaporization/excitation laser. Temporal resolution of Pb atomic fluorescence from the background plasma emission permitted very sensitive detection ($Pb_{LOD}=$ 47 $ng/m^3$). Low analytical duty cycles (limited by laser repetition rate) and single-element operation of the system were acknowledged as limitations, though the high level of selectivity and possibility for miniaturization were seen as positive features.

Direct (vacuum) inlets are versatile means of introducing ambient or collected particles. In the majority of such systems, differentially pumped momentum separators (often called particle beam interfaces) provide the means for performing analysis by methods requiring vacuum environments (i.e., mass spectrometry) and optionally identification/analysis of single particles in real-time (7). The research groups of Prather (8–11), Johnston (12–14), and Ramsey (15–16) have each made unique contributions to the field.

Prather and co-workers (9–11) have described the use of aerodynamic particle sizing using a dual-laser triggering system followed by laser vaporization/ionization and time-of-flight mass spectrometry (TOF-MS). One possible implementation of this time-of-flight mass spectrometry device is described in U.S. Pat. No. 5,681,752 to Prather. The production of both positive and negative ion species has been used to advantage in gaining comprehensive information from single aerosol particles.

Johnston (12–14) has used the intensity of scattered laser radiation as a measure of particle size and as a trigger for subsequent laser vaporization/ionization and TOF-MS analysis. One possible implementation of this time-of-flight mass spectrometry device is described in U.S. Pat. No. 5,565,677 to Wexler et al.

Ramsey and co-workers (15, 16) have exploited the ability of quadrupole ion traps to operate in modes which either trap charged particles or perform mass analysis of laser-produced ions. In the former mode of operation, charged particles can be effectively levitated within the three dimensional trap. Use of the ion trap as a mass analyzer provides higher levels of chemical information than TOF-MS as collision-induced dissociation (MS/MS) of isolated ions can be performed. Similarly, Davis and co-workers have used electrodynamic traps as a means of isolating charged particles at atmospheric pressure for interrogation by Raman spectroscopy (17).

Chemical analysis of batch-type (not single particle) particulate samples most often involves collection of samples via directed flow through a quartz fiber filter having pore sizes on the order of 1 $\mu$m (18–23). Optical scattering or differential mobility particle sizing can be accomplished prior to deposition on the filter. Very different from the case of single particle analysis, batch chemical analysis is very seldom performed in real-time or on-site (remotely). Accordingly, issues of sample turnaround time, loss of temporal resolution, and possible sample loss or contamination are amplified.

Immobilized particles can be analyzed non-destructively via x-ray fluorescence (XRF) or particle induced x-ray emission (PIXE) (18). X-ray fluorescence analysis involves relatively simple instrumentation, is highly automated, and provides high sample throughput. Insensitivity to low Z elements and matrix effects due to differences in particle morphology can be limiting in some cases. Spectrochemical analysis by inductively coupled plasma atomic emission and mass spectrometries (ICP-AES/MS) has been applied to collected particulate matter in a number of fashions (19–24). Acid dissolution followed by solution nebulization is straightforward from the point of view of calibration and matrix normalization (19, 20). Small collected sample masses and general difficulties in achieving quantitative dissolution make this approach susceptible to contamination and challenge available detection limits. Laser ablation (LA) directly from the filter surface is an attractive approach to sample introduction for ICP-AES/MS analysis (21–23). Tanaka and co-workers (21) have demonstrated the use of standard solutions deposited on filter substrates as a very powerful means of quantification for LA-ICP-MS.

Collection of particulates via electrostatic precipitation has also been shown to provide a convenient means of presenting samples to atmospheric pressure plasmas (24). Bitterli et al. (24) have used a hollow graphite collector which can in turn be placed in an electrothermal vaporizer assembly in a manner similar to graphite furnace atomizers used for sample introduction to ICP-MS.

As a final example of filter collection for subsequent plasma source analysis, a commercially available plasma system (PT-1000, Yokagawa Electric Corporation, Tokyo) uses pneumatic transport to sweep particulate matter to a microwave-induced plasma (MIP) sustained with helium as the discharge gas (25, 26). Particles entering the plasma are thermally dissociated, and the emission from up to four analyte elements is monitored by separate monochromators. Particle size distributions are extrapolated from the total of the analyte emission responses based on a diameter-cubed relationship and the assumption that the particles are spherical in shape.

Related to the work described here is the application of a low pressure, glow discharge (GD) as an atomization and ionization source for collected particulate matter. Van Grieken and co-workers (27) mounted a metal target at the base of an impactor apparatus to collect airborne particles. The target was then mounted in the ion volume of the VG9000 glow discharge mass spectrometer system. Because the particle samples are electrically nonconductive in nature, a portion of the metal target was exposed to the plasma region to initiate the discharge such that the powders were sputtered from the surface, the constituent elements ionized within the negative glow, and then identified by their isotopic abundances. The collected particles were distributed in an approximately 2 millimeter diameter, cone-shaped mound of 50 to 90 micrometers height. The sample analysis times were on the order of 30 to 60 minutes, at which point the mass spectra were composed only of the species present in the target metal. Limits of detection were estimated to be in the low to sub-ppm level relative to the total sample mass. However, approximate masses of the sample sizes were not provided.

It is important to recognize that, while there are a plethora of applications wherein real-time particle sizing is performed on flowing streams, there is a scarcity of methodologies which accomplish elemental (much less molecular) species analysis in the continuous, batch-type mode of operation.

OBJECTS AND SUMMARY OF THE INVENTION

It is a principal object of the present invention to provide apparatus and methods employing low pressure plasmas for sampling, analyzing and characterizing particulate matter, both airborne and collected.

It is also a principal object of the present invention to provide apparatus and methods employing technology that employs a device for producing a low pressure plasma for sampling, analyzing and characterizing of particulate matter, both airborne and collected.

It is also a principal object of the present invention to provide apparatus and methods employing glow discharge technology for analyzing and characterizing of particulate matter (both airborne and collected) in the batch-type mode of operation as opposed to single particle methods.

It is another principal object of the present invention to provide apparatus and methods employing glow discharge technology for elemental species analysis of airborne particulate matter in the batch-type mode of operation.

It is a further principal object of the present invention to provide apparatus and methods employing glow discharge technology for molecular species analysis of airborne particulate matter in the batch-type mode of operation.

It is still another principal object of the present invention to provide apparatus and methods employing glow discharge technology for direct, remote monitoring of airborne particulate matter both in real time and particles collected in situ.

It is yet another principal object of the present invention to provide apparatus and methods employing glow discharge technology for direct, remote exhaust stack monitoring of airborne particulate matter both in real time and particles collected in situ.

It is a still further principal object of the present invention to provide apparatus and methods capable of a batch-type mode of operation and employing glow discharge technology for analyzing and characterizing of particulate matter as well as the gaseous components in which the particulate matter is entrained.

It is a still further principal object of the present invention to provide apparatus and methods for analyzing particulate matter in a particle beam (PB) subjected to low-power laser scattering to effect particle size analysis and introduced into low pressure (glow discharge) plasma sources for subsequent real time analysis by atomic emission and mass spectrometry.

Additional objects and advantages of the invention will be set forth in part in the description which follows, and in part will be obvious from the description, or may be learned by practice of the invention.

To achieve the objects and in accordance with the purpose of the invention, as embodied and broadly described herein, the apparatus and methods of the present invention implement a particle beam (PB) sampling scheme for the introduction of particulate matter into low pressure (glow discharge) plasma sources for subsequent atomic emission and mass spectrometry chemical analysis in real time, whether the particles are provided in a continuous stream during the analysis or are collected (in situ or ex situ) and analyzed periodically upon obtaining a suitable number of particles to be analyzed.

The apparatus and methods of the present invention include a device for producing a low pressure plasma (e.g., a glow discharge unit), a momentum separator (also known as a particle beam interface), and a conduit.

The device for producing a low pressure plasma has a particle input port configured and disposed for receiving particles to be analyzed. The device provides the energy that ionizes and excites the particles and has at least one sampling region where ionized and/or excited particles are to be analyzed. In the glow discharge embodiment of the device for producing a low pressure plasma, particles enter the source volume and impinge on the heated walls (200 to 1000° C.) of the source volume and are flash vaporized. The resultant atoms/molecules are subjected to collisions that result in excitation and ionization in the sampling region of the low pressure plasma. The glow discharge sources operate at pressures of between 0.5 and 10 Torr (in the presence of inert gases like helium or argon) and at powers of less than 100 Watts. The sustaining power could be in the form of direct current, radio frequency or microwave regions of the electromagnetic spectrum. Atomic emission analysis provides information about the elements present in the composition residing in the sampling region, while mass spectrometry, which may be performed simultaneously with the atomic emission analysis or separately, provides information about both the elements present in the composition and the molecular species present in the composition that resides in the sampling region. Real-time particle sizing through light scattering methods such as a low-power laser scattering device can also be readily achieved. Real-time analysis of the gaseous components that entrain the particles delivered by the conduit to the momentum separator can also be readily achieved by the apparatus and methods of the present invention.

Particle beam interfaces such as momentum separators are an efficient means of introducing particulate matter through "vacuum" action (two roughing pumps). A momentum separator has a particle exit port connected in communication with the particle input port of the glow discharge unit or other device for producing a low pressure plasma. The momentum separator has a particle entrance port connected in communication with the particle exit port.

The conduit is a hollow tube that has an entrance opening on one end and an exit opening on the opposite end. The exit opening of the conduit is connected to the entrance port of the momentum separator. The conduit functions to provide a path for directing and transporting to the momentum separator, the gaseous matter that contains the entrained particulate matter that is to be analyzed. One embodiment of the conduit takes the form of a sniffer that includes a restricted flow portion.

It is believed that this general approach holds much promise as process monitoring needs and federal regulations require further chemical information beyond the present particle size standards. The use of vacuum sample introduction, low plasma powers in the glow discharge unit, and small size (less than a shoebox), suggest applications wherein introduction of discrete (collected) samples or continuous remote monitoring can be easily envisioned. The most obvious application of any such methods would be in direct, remote exhaust stack monitoring.

The accompanying drawings, which are incorporated in and constitute a part of this specification, illustrate several embodiments of the invention and, together with the description, serve to explain the principles of the invention.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

Figure 1:
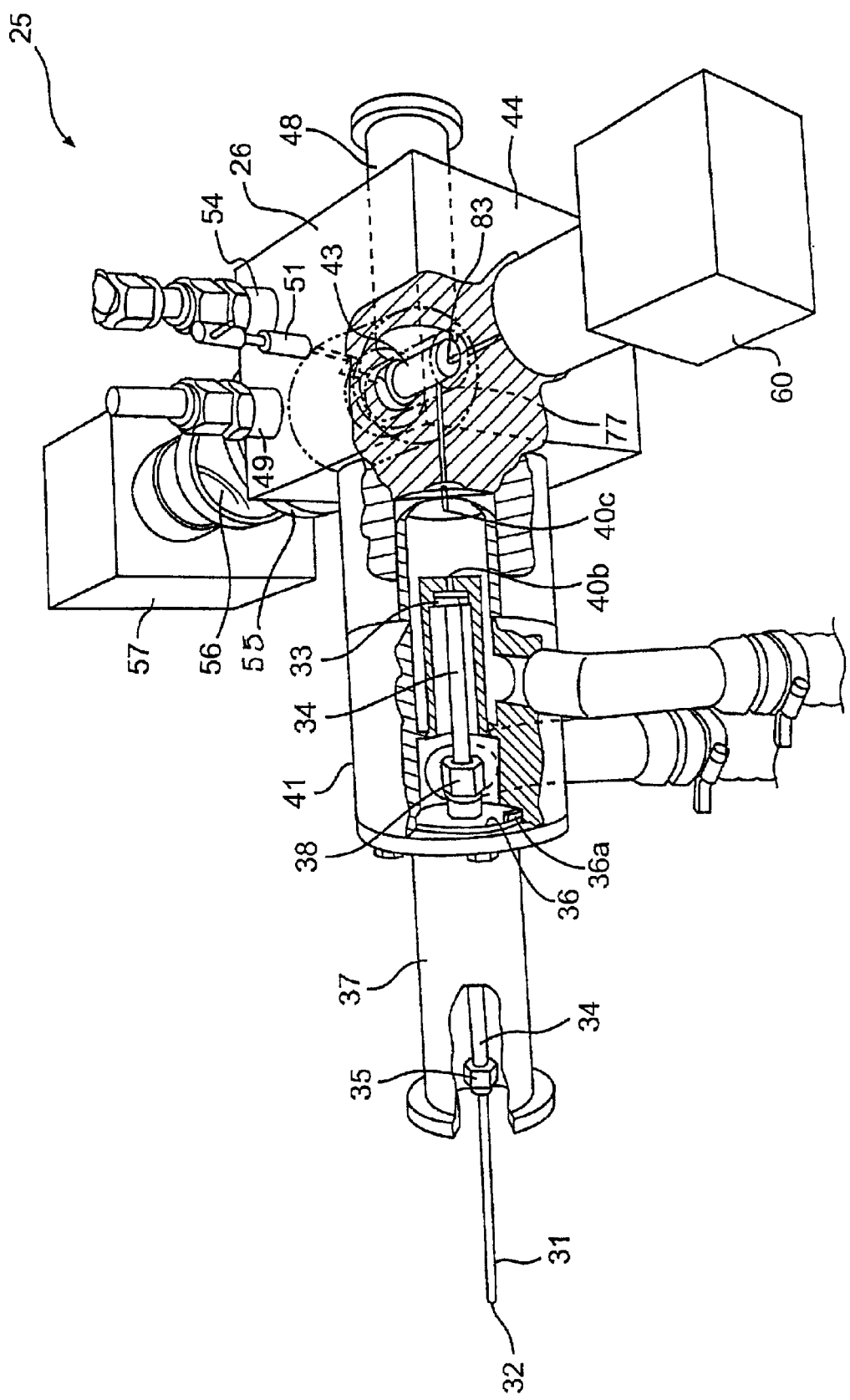
FIG. 1 shows in a perspective view that is partially cut away, a presently preferred embodiment of the PB-GD apparatus of the present invention configured to perform atomic emission analysis and mass spectrometry analysis of airborne particles taken from an ambient pressure environment.

A presently preferred embodiment of the PB-GD apparatus of the present invention is configured with the capability of simultaneously performing atomic emission analysis and mass spectrometry analysis of airborne particles taken from an ambient pressure environment or a sub-ambient pressure environment, and this feature is shown in an embodiment that is represented generally by the numeral 25 and depicted in a perspective view that is partially cut away in FIG. 1.

Various configurations, sub-assemblies and components of the particle beam-glow discharge (PB-GD) sampling and analysis apparatus are shown in FIGS. 1–8 for example, and among the basic components are a conduit, a momentum separator and a device for producing a low pressure plasma.

Figure 3:
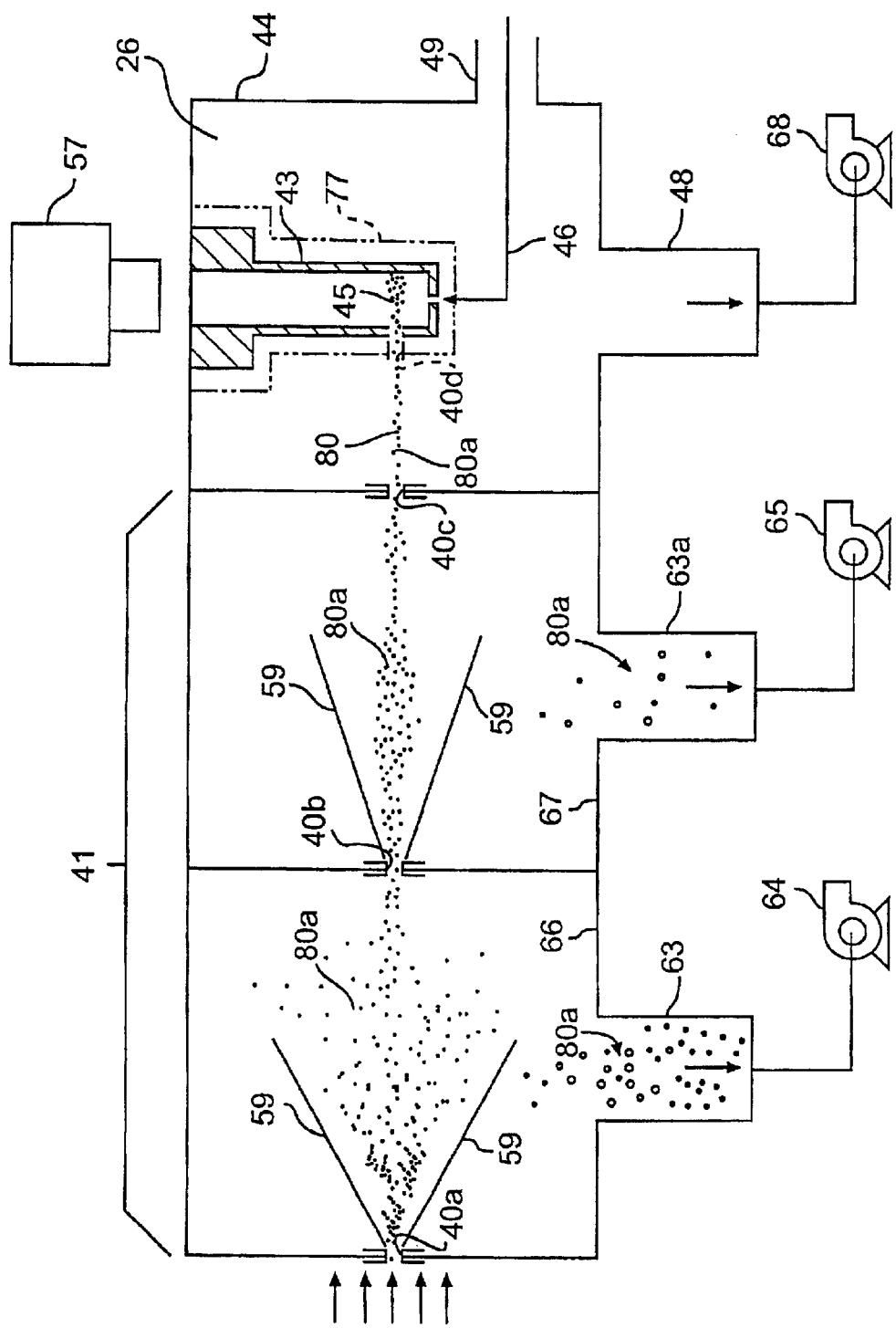
FIG. 3 schematically illustrates a presently preferred embodiment of the particle beam-glow discharge (PB-GD) sampling and analysis apparatus of the present invention configured to perform atomic emission analysis of airborne particles taken from an ambient pressure environment.
Figure 21:
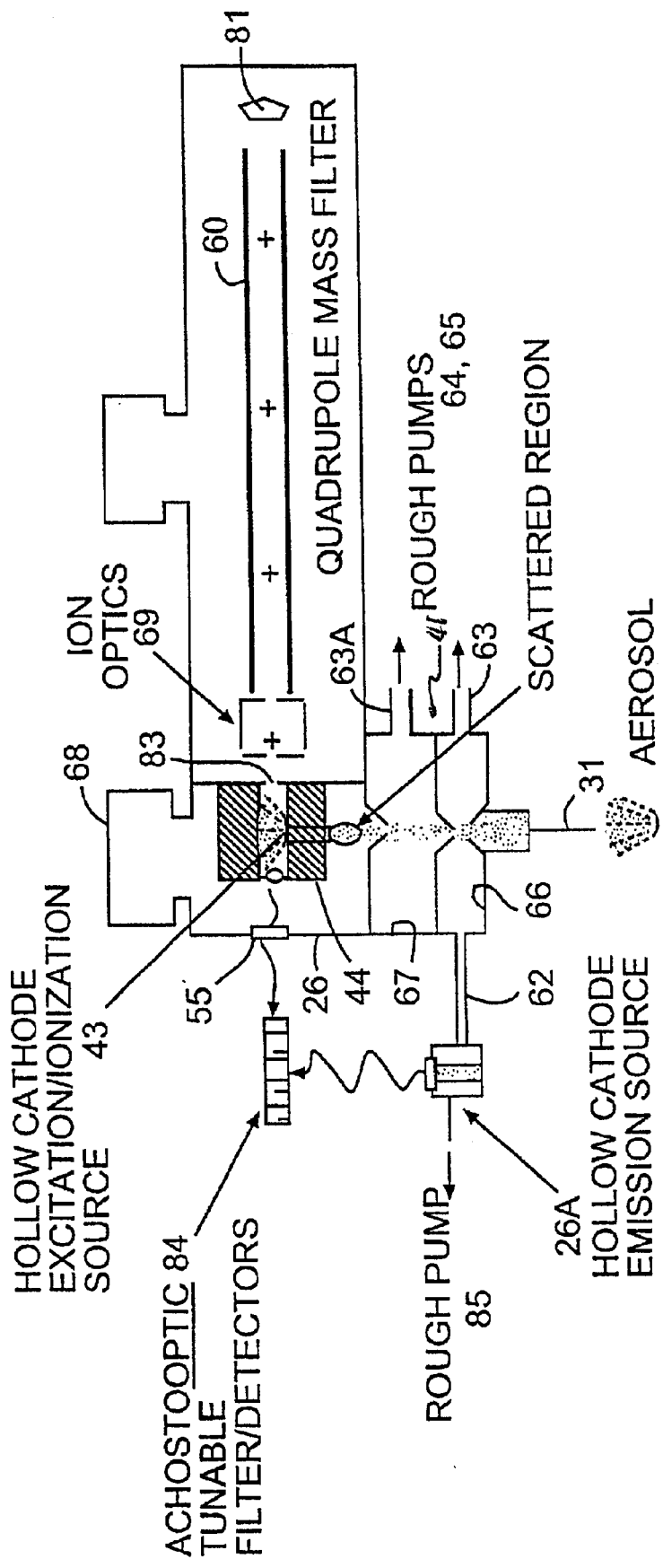
FIG. 21 is a schematic diagram of an embodiment of the present invention configured to provide chemical analysis via atomic emission spectrometry and mass spectrometry and particle size analysis by laser light scattering.

As shown schematically in FIGS. 3 and 21, one presently preferred embodiment of a momentum separator 41 (also called a particle beam (PB) interface 41) employs direct drive rotary pumps 64, 65 (also known as roughing pumps) to evacuate adjacent successive chambers 66, 67 via respective pipes 63, 63a. This is a two stage embodiment of a momentum separator 41, as it employs two successive chambers 66, 67. However, while not separately illustrated, a single stage embodiment of a momentum separator 41 is also contemplated and would have only one chamber 66 or 67 connected to one pump 64 or 65 via one pipe 63 or 63a.

Figure 5A:
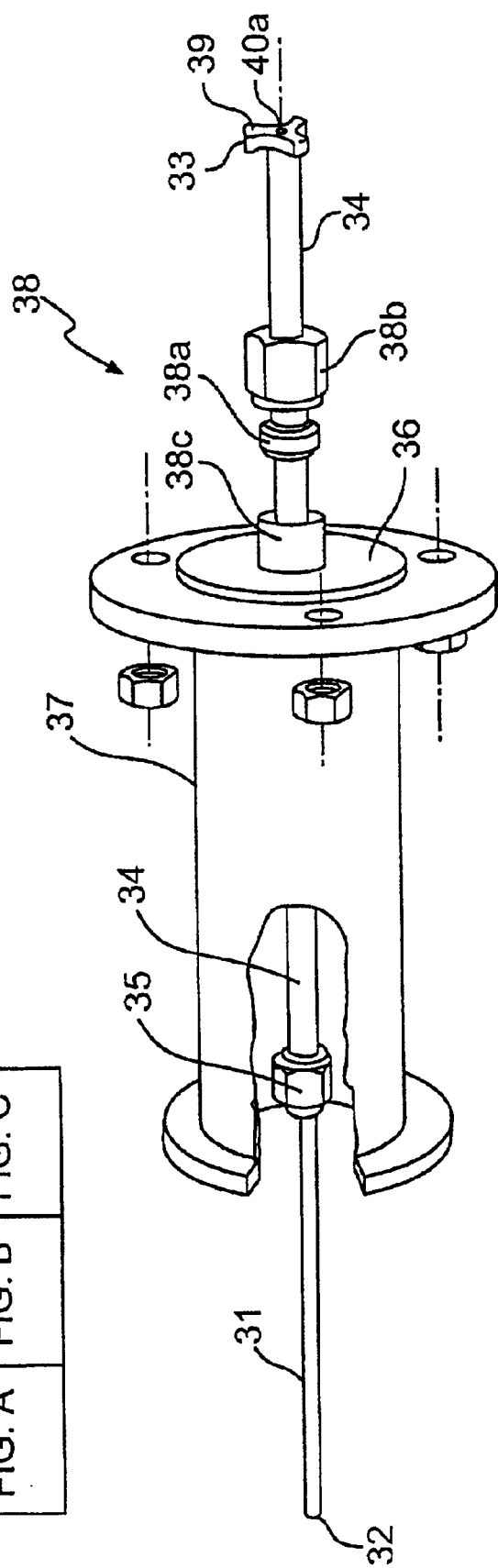
FIG. 5A shows in a perspective view that is partially cut away, a first assembly of the momentum separator of the embodiment of the PB-GD apparatus shown in FIG. 1.

As shown in FIG. 5A, the free end of a first nozzle 33 defines a forward surface 39. As shown in FIGS. 3 and 5A, a particle entrance port 40a of the momentum separator 41 is defined through first nozzle 33 and in forward surface 39 of first nozzle 33. The diameter of particle entrance port 40a is desirably about 1 mm or ¹⁄₁₆ inch. As shown in FIG. 3, an intermediate port 40b of momentum separator 41 communicates with entrance port 40a and is spaced axially and concentrically from entrance port 40a. As schematically shown in FIG. 3 by the diverging chain-dashed lines labeled 59, many of the atoms and molecules (typically gases)

accompanying particles 80a entering chamber 66 do not enter intermediate port 40b and are sucked out of chamber 66 by pump 64 via pipe 63.

Figure 5B:
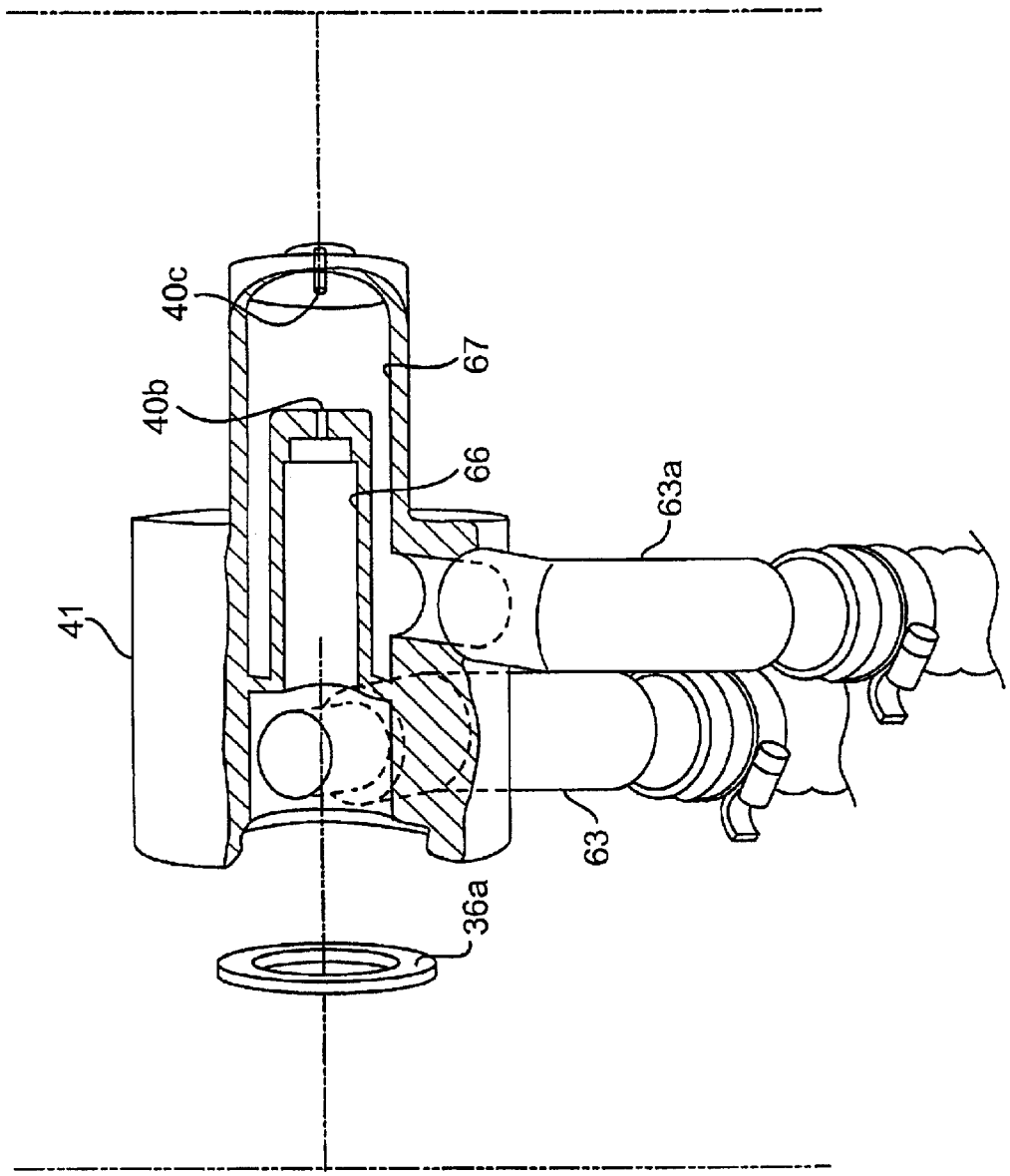
FIG. 5B shows in a perspective view that is partially cut away, a second assembly of the momentum separator of the embodiment of the PB-GD apparatus shown in FIG. 1.

Because the illustrated momentum separator 41 is a two stage embodiment, it further includes a particle exit port 40c connected in communication with intermediate port 40b and entrance port 40a. As shown in FIGS. 3 and 5B, particle exit port 40c is spaced axially and concentrically from intermediate port 40b. As shown in FIG. 3, a beam 80 of particles 80a emerges from momentum separator 41 via particle exit port 40c. As schematically shown in FIG. 3 by the diverging chain-dashed lines labeled 59, many of the atoms and molecules accompanying particles 80a entering chamber 67 do not leave chamber 67 via exit port 40c and are sucked out of chamber 67 by pump 65 via pipe 63a.

Figure 4:
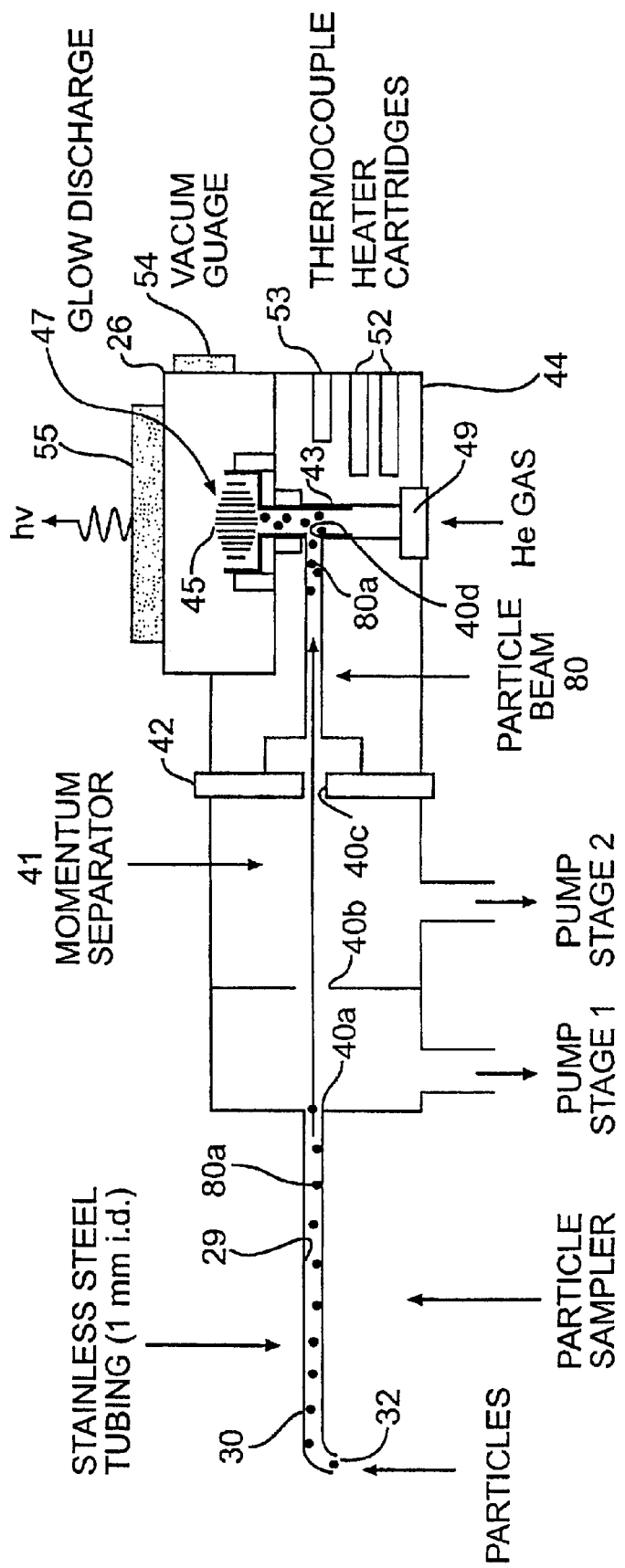
FIG. 4 is a diagrammatic representation of a presently preferred embodiment of a particle beam-hollow cathode atomic emission spectroscopy (PB-HC-AES) apparatus of the present invention.

As schematically shown in FIGS. 3 and 4, particles 80a pass through two stages of differential pumping across a pair of 1 mm diameter orifices 40a, 40b that are spaced 10 mm apart in the illustrated two stage embodiment of momentum separator 41. The momentum separator 41 acts to "skim" lightweight gases and fine particles from the particle flow and reduce the pressure in the system beyond exit port 40c to less than 0.01 Torr.

Suitable momentum separators for use in the apparatus of the present invention include those employed in the Thermabeam™ particle beam LC-MS system (Extrel Corporation, Pittsburgh, Pa.), with the skimmer geometry unchanged for this application. Based on earlier studies (32) performed on aerosol samples, this particular system quite readily transports particles in the 0.1 micrometer to 10 micrometer size range into the device for producing a low pressure plasma.

Figure 6:
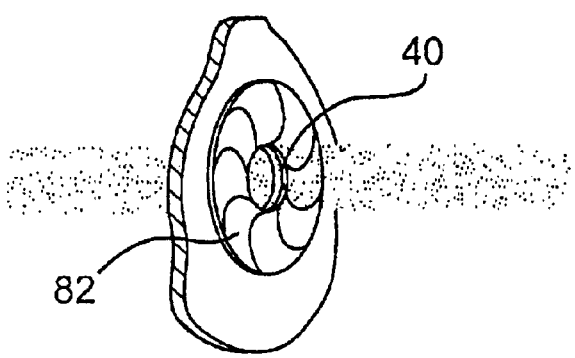
FIG. 6 presents a schematic representation of adjustable apertures provided in the momentum separator component of a presently preferred embodiment of the PB-GD apparatus of the present invention.

Moreover, it is known that such momentum separator systems can be designed to pass targeted ranges of particle sizes. As schematically represented in FIG. 6, the size of each orifice 40 of ports 40a, 40b and 40c of momentum separator 41 typically ranges from 0.5 to 2.0 mm. Each orifice 40 can be varied by expanding or contracting the diaphragm 82 that defines each port 40a, 40b and 40c. The axial spacing between ports 40a and 40b and between ports 40b and 40c is desirably about 10 mm. However, the spacing of the ports 40a, 40b and 40c and the speed of the pumps 64, 65 can also be changed so as to change the range of particle sizes that pass through the momentum separator 41.

As schematically shown in FIG. 4, a conduit 30 can take the form of a hollow tube defining an internal passage 29. At the free end of the conduit 30 there is an entrance opening 32 that the user can locate wherever the particles that are to be transferred to the low pressure plasma reside. For example, the particles targeted for analysis may be collected in a vial or on a filter sheet as well as being carried in an airborne gaseous mixture or in a sub-atmospheric pressure environment, an example of the latter being in a reactor for manufacturing silicon wafers or other materials. The configuration of the conduit 30 and its entrance opening 32 must permit the user to dispose the entrance opening 32 in locations where the particles can be sucked into the conduit 30 and transferred to the momentum separator 41. Thus, the entrance opening 32 of conduit 30 can be configured in different shapes and opening sizes depending on the source of the particles that are to be sampled.

As schematically shown in FIG. 4 for example, the end of the conduit 30 disposed opposite the entrance opening 32 has an exit opening that is connected to the entrance port 40a of the momentum separator 41, and thus the conduit 30 functions to provide a path for directing and transporting to the momentum separator 41, the particles 80a that are to be analyzed. In the portion of the conduit adjacent the momentum separator, the internal passage 29 of the conduit 30 desirably should provide a straight line path into the entrance port 40a of the momentum separator 41. Desirably, as shown in FIG. 4 for example, the passage 29 defined within the conduit 30 is uniform as it approaches the entrance port 40a of the momentum separator 41 and has the same diameter as the entrance port 40a of the momentum separator 41.

The pumps 64, 65 of the momentum separator 41 provide the suction that draws the particulate matter 80a and any associated gaseous components into the entrance opening 32 of conduit 30. Once inside the conduit 30, the particulate matter 80a forms into a stream along with the gaseous components, and this stream of particulate matter 80a and gaseous components is transported within the internal passage 29 of the conduit 30 to the entrance port 40a of the momentum separator 41. In effect, the conduit 30 functions like the hose attachment of a vacuum cleaner, and the vacuum pumps 64, 65 of the momentum separator 41 provide suction like the vacuum cleaner. Thus, the user can dispose the entrance opening 32 of the conduit 30 wherever there are particles and/or gases to be sampled and analyzed. The relatively small size of the conduit's entrance opening 32 provides enough suction to draw the particles and surrounding gases into the momentum separator and ultimately introduce the particles themselves into the device for producing the low pressure plasma where the particles can be analyzed.

The effective flow diameter (d) of the conduit 30 is defined as the diameter that would yield the flow area of the internal passage 29 of the conduit 30 as if the flow area of the internal passage 29 of the conduit 30 had a circular perimeter. For example, if the cross-sectional area (A) of the internal passage 29 (regardless of the shape of its perimeter) is 12 square millimeters, then the effective flow diameter (d) for this area (A) is calculated as $d=2\%(A/\pi)=2\%(12/3.1416)=2(1.95)=3.9$ mm.

The exit opening of the conduit 30 is desirably configured with the same effective flow diameter (and area) as the entrance port 40a of the momentum separator 41 and connects directly to the entrance port 40a of the momentum separator 41 in a continuous fashion, which means that the shape of the exit opening of the conduit 30 is desirably the same as that of the entrance port 40a of the momentum separator 41. This avoids any turbulence in the flow at the transition from the conduit 30 to the momentum separator 41.

Moreover, conduit 30 desirably can include a restrictive flow portion disposed between the conduit's entrance opening 32 and the entrance port (40a) of momentum separator 41. Desirably, as schematically shown in FIG. 4 for example, the effective flow diameter of the internal passage 29 of the conduit 30 is uniform throughout its length and the same as the effective flow diameter of entrance port 40a of momentum separator 41 and forms a continuous restrictive flow portion. This uniform effective flow diameter is typically about one millimeter. However, it is believed that the restrictive flow portion of conduit 30 can include an effective flow diameter in the range of about 0.5 to 4.0 millimeters and still achieve useful results.

As shown in FIG. 1 for example, one embodiment of the conduit 30 can include a so-called "sniffer," which is a restricted flow tube that is provided in the form of a hollow stainless steel tube 31 having an internal passage 29 of constant effective flow diameter running along the entire length of the inside of the tube. The diameter of the internal passage of the sniffer 31 and of the entrance opening 32 of sniffer 31 is desirably the same as the diameter of the entrance port 40a of the momentum separator 41. Typically, the diameter of the internal passage 29 of sniffer 31 is about one (1) millimeter or one-sixteenth (1/16) of an inch. The length of sniffer 31 can be about 4 inches. In a sniffer 31 with a cylindrical outside surface and an internal passage of 1 mm in diameter, the outside diameter is suitably 1.6 mm.

The effective diameter of the internal passage 29 of the conduit 30 can vary somewhat along its length and the effective diameter of the conduit's exit opening also can differ from the effective flow diameter of the entrance port 40a of the momentum separator 41 without completely preventing the achievement of useful results. In the embodiment shown in FIG. 1 for example, this internal effective flow diameter of the conduit 30 can measure one (1) millimeter over the sniffer 31 portion of the length and 4.5 millimeters over an intermediate portion 34 of the conduit's length, before connecting to the momentum separator's first nozzle 33, which defines the entrance port 40a of the momentum separator 41 and has an internal effective diameter of one (1) millimeter.

As shown in FIG. 1, the conduit 30 can also include a stainless steel hollow tube 34. As shown in FIG. 5A for example, the end of sniffer 31 that is opposite entrance opening 32 is connected via a first threaded pressure fitting 35 to a 6.5 mm outside diameter stainless steel hollow tube 34. In this two piece embodiment, the exit opening of the conduit 30 is defined by the exit opening of tube 34, which is connected to first nozzle 33 of momentum separator 41. As shown in FIG. 5A for example, tube 34 is mounted to a flange 36 of a cylindrical protective housing 37 of the sniffer attachment assembly via a second pressure fitting 38 that includes a compressible, annular washer 38a, disposed between a second threaded nut 38b and a threaded bushing 38c of flange 36. Sniffer attachment housing 37, while not a necessary component to the operation of the present invention, shields first fitting 35 and tube 34 from jostling. Moreover, as shown in FIG. 1, the sniffer attachment assembly is connected to momentum separator 41 via flange 36 and sealing gasket 36a, which is also shown in FIG. 5B.

Glow Discharge Atomic Emission Spectroscopy—In further accordance with the present invention, a device 26 for producing a low pressure plasma can take the form of a glow discharge unit, an electrode-less discharge lamp, or an inductively coupled plasma. Components of the particle beam-glow discharge (PB-GD) sampling and analysis apparatus of the present invention configured to perform atomic emission analysis of particulate matter are shown in FIGS. 1–4 for example. As schematically shown in FIG. 4, the low pressure plasma generator device 26 has a particle input port 40d that is configured and disposed for receiving particles to be analyzed, either with or without gaseous components. For the sake of convenience, this illustrative discussion will confine its references to a glow discharge unit 26. As schematically shown in FIG. 4, the glow discharge unit 26 has at least one sampling region 47 where particles 80a are to be analyzed.

Figure 5C:
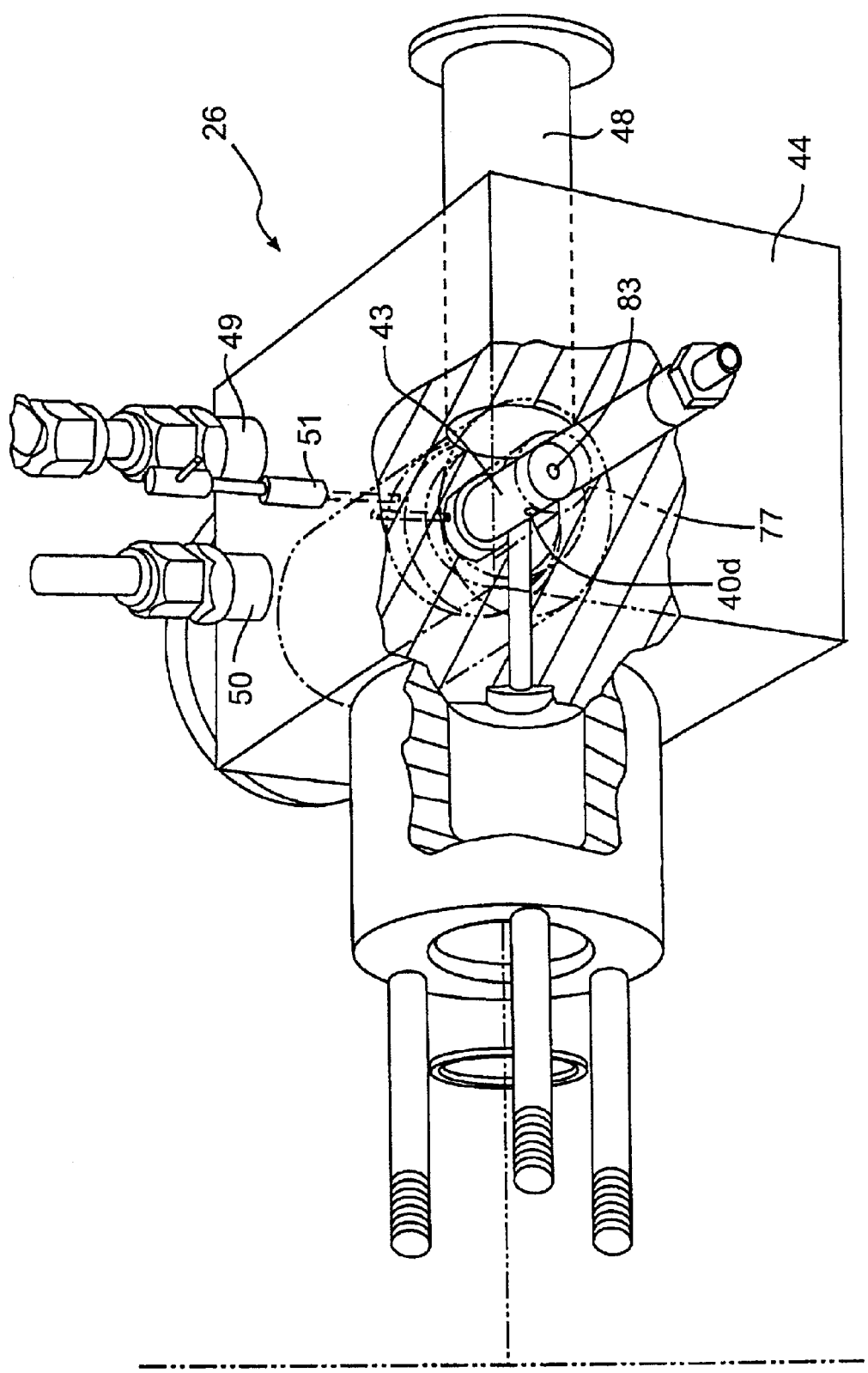
FIG. 5C shows in a perspective view that is partially cut away, a third assembly of the momentum separator and glow discharge cell of the embodiment of the PB-GD apparatus shown in FIG. 1.

As schematically shown in FIG. 4, the momentum separator 41 is mounted via a flange 42 to the same hollow cathode plasma source 26 that has been used previously for atomic emission source (AES) analysis of solution samples (29–32). As shown in FIGS. 4 and 5C, a hollow cathode (HC) 43 formed of stainless-steel is mounted at the center of a stainless-steel "thermoblock" 44 that ensures easy access to the plasma for optical monitoring. As shown in FIGS. 1, 2, 3, 5C and 8 for example, an insulating sleeve 77 (outlined in chain-dashed lines) is disposed to electrically insulate thermoblock 44 from hollow cathode 43. Sleeve 77 may be suitably formed of polytetrafluoroethelyne (PTFE) for example.

Figure 2:
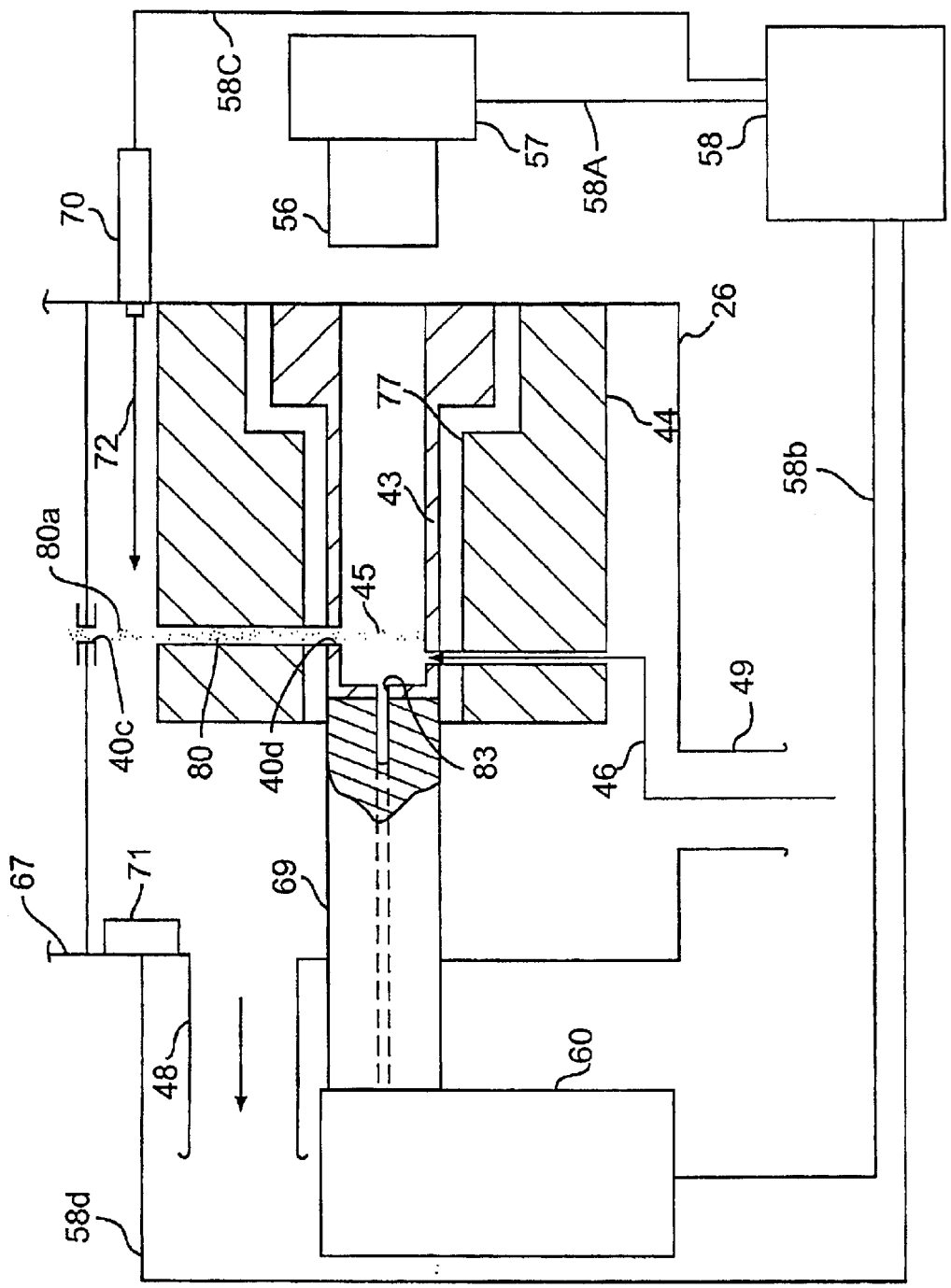
FIG. 2 presents in a diagrammatic view, a presently preferred alternative embodiment of the PB-GD apparatus of the present invention configured to perform particulate size analysis, atomic emission analysis and mass spectrometry analysis of airborne particles taken from an ambient pressure environment.

As schematically shown in FIGS. 2 and 4, the analyte material 45 is introduced through a 2 mm diameter opening 40d in the side of the 25 mm long, 7 mm diameter stainless steel hollow cathode 43. As schematically shown in FIG. 4, the analyte material 45 is vaporized and swept by the helium (He) flow, which is schematically indicated in FIG. 2 by the right angled arrow designated by the numeral 46, further into the hollow cathode plasma 47 (FIG. 4) for subsequent excitation of atomic species.

As shown in FIG. 5C, the glow discharge embodiment of device 26 can include a source vacuum port 48, a discharge gas inlet 49, a pressure gauge coupling 50, and electrical feedthroughs 51, which are also placed on thermoblock 44. As shown in FIG. 4, the heating components 52 are also placed on the thermoblock 44. The entire thermoblock assembly 44 is desirably heated by a pair of cartridge heaters (Model SC 3618K 423, Scientific Instrument Services, Ringoes, N.J.) to promote sample vaporization and atomization, with the block temperature monitored by a W-Re thermocouple 53. The Helium discharge gas pressure within the hollow cathode source 26 is monitored by a thermocouple vacuum gauge 54 such as a model DV-24 available from Teledyne Hastings-Raydist of Hampton, Va.).

The low pressure plasma 26 may be powered by either direct current, microwave or radio frequency power supplies. For example, a hollow cathode glow discharge source 26 can be powered by a Bertan (Hicksville, N.Y.) Model 915-1N power supply (not shown), operating in a current-controlled mode, over the range of zero to 100 milliamperes.

As shown in FIGS. 1 and 2, the atomic emission from the glow discharge unit 26 is analyzed by an instrument such as a monochromator 57. As shown in FIG. 1, the atomic emission (schematically indicated by the squiggly arrow designated hv) from the glow discharge unit 26 can be sampled through a fused silica window 55. As shown in FIG. 1, a plano-convex fused silica lens 56 (45 millimeters diameter, 10 centimeters focal length) can be used to focus the image of the excitation region 47 (FIG. 4) approximately one-to-one (1:1) on the entrance slit (not shown) of a monochromator 57. An example of a suitable monochromator 57 is provided by a 0.24 meter Czerny-Turner spectrometer equipped with a 2400 grooves/millimeter holographic grating (Digikrom 240, CVI Laser Corp., Albuquerque, N. Mex.). Monochromator 57 is applied for optical monitoring, with the scanning range, slit width, spectral calibration and wavelength selection adjusted via the monochromator control interface.

The atomic emission signals detected by a photomultiplier tube (Hamamatsu Model R955, Bridgewater, N.J.) are converted into voltage signals with an analog current meter. As schematically shown in FIG. 2, a computer 58 such as a Macintosh IIsi computer is employed to record the output of the current meter via a National Instruments (Austin, Tex.) NB-MIO-16X interface board. The exchange of signals between computer 58 and monochromator 57 is schematically indicated in FIG. 2 by the connecting line designated 58a. Due to the transient nature of the particle introduction, an X-Y recorder type program within the National Instruments' LabView 2 software environment has been developed to record the data. The transient optical data are processed and managed in the form of Microsoft (Seattle, Wash.) EXCEL files.

The momentum separator and hollow cathode atomic emission spectrometry (HC-AES) coupling is very similar to the arrangement used for element-specific liquid chromatography (LC) detection (29–31). However, the configuration of the present invention differs from the LC detection arrangement in that a 1.6 mm o.d. stainless steel sniffer 31 has been mounted in the place of the nebulizer and spray chamber of the LC detection arrangement. In the configuration for LC detection, a thermoconcentric nebulizer and heated spray chamber act in concert to form a fine aerosol, which is desolvated such that dry particles are directed through the particle beam interface 41. In the LC detection arrangement, the particle beam interface strips away the moisture from the nebulized solution to yield the dry particles forming the particle beam. The present invention recognizes that a nebulized solution is in some sense a wet particle. Thus, in the present invention, the particle beam interface can be used to remove gaseous components from particles in an effluent rather than removing moisture from a nebulized solution. One possible implementation of a particle beam interface 41 is described in U.S. Pat. No. 5,565,677 to Wexler et al., which is hereby incorporated herein by this reference.

Glow Discharge Mass Spectrometry—As shown in FIGS. 1 and 2, mass spectrometric analysis of introduced particulate matter can be undertaken on a commercial particle beam LC-MS instrument 60 such as a Benchmark brand instrument available from Extrel Corporation, Pittsburgh, Pa. In this implementation of direct particle introduction shown in FIG. 1 for example, the conduit apparatus 30 including "sniffer" 31 replaces the commercial nebulizer and desolvation chamber systems that characterize the implementation for liquid chromatography detection.

Figure 7:
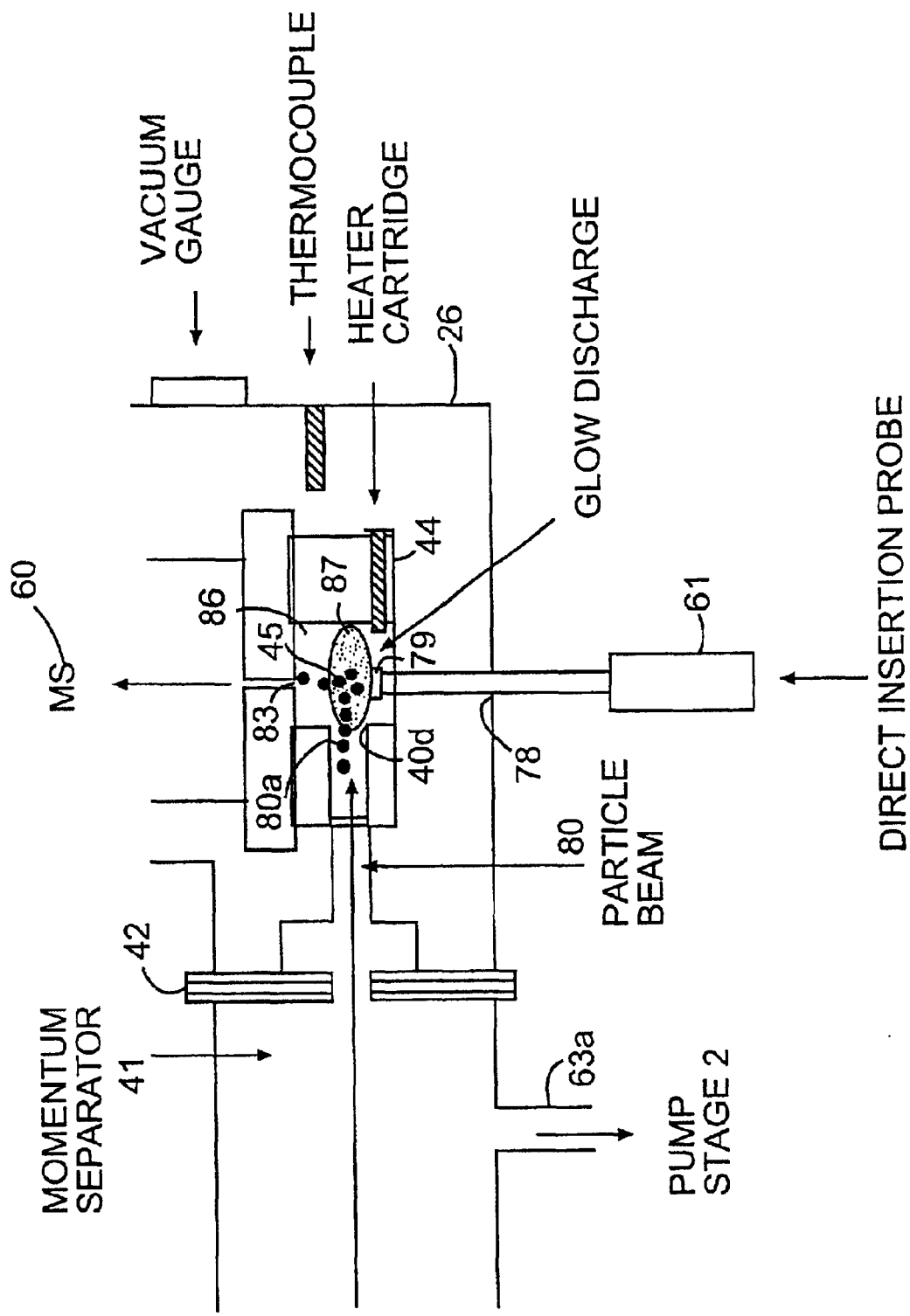
FIG. 7 is a diagrammatic representation of the presently preferred embodiment of the particle beam-glow discharge mass spectrometry (PB-GDMS) complement of the atomic emission apparatus of FIG. 4.

The commercial LC-MS system was modified by replacing the conventional electron impact source volume with a glow discharge source 26 of the same outer geometry, as shown in FIG. 7. In simple terms, as schematically shown in FIG. 7, a 12.5 mm diameter direct insertion probe 61 (DIP) designed for glow discharge mass spectrometric (GDMS) analysis of metallic samples (33) was inserted through the "solids probe" inlet 78 and perpendicular to the path of the incoming particles 80a in the particle beam 80. In this way, as shown in FIG. 7 for example, a 4 millimeter diameter copper target 79 (i.e., the planar-shaped cathode in the glow discharge plasma source) was introduced to the mass spectrometer chamber and in communication with the ion volume 86. Particles impinging on the heated ion volume wall dissociate and diffuse into the plasma negative glow region 87. As schematically shown in FIG. 2 for example, analyte species 45 ionized through collision with electrons or metastable argon (Ar) species are sampled through a one millimeter exit aperture 83 (FIGS. 5C and 7) that leads to the quadrupole mass analyzer 60. The exchange of signals between computer 58 and mass spectrometer 60 is indicated schematically in FIG. 2 by a connecting line designated 58b.

It is important to note the differences (at present) in the discharge geometries between the atomic emission source (hollow cathode) and the mass spectrometry source (planar cathode). The GDMS ion source operates under a different set of conditions than the hollow cathode source, with the latter geometry having a number of fundamental advantages. The GDMS plasma is desirably powered by a Spellman brand (Plainview, N.Y.) Model RHR5N50 d.c. power supply operating in the constant current mode, at nominal currents of 0.5 B 2.5 milliamps and potentials of 600 B 1000 Volts. While difficult to measure directly, the argon plasma gas pressure was in the range of 0.5 to 1.0 Torr for the experiments described here. The Benchmark™ mass spectrometer system operates under the control of a computer such as a Sun SPARCstation® (Sun Microsystems, Inc., Mountain View, Calif.) using the Extrel IONstation® software package. While the instrument is capable of both positive and negative ion analysis, only positive ion detection was employed here. Negative ion mass spectrometry is seen as an area of great potential for the GDMS analysis of particulate matter as ions of both polarities are produced in a continuous fashion in the plasma (34).

Chemicals—Two types of samples were used to evaluate the feasibility of the PB-GD approach to direct particle analysis. NIST SRM 1648, Urban Particulate Matter (UPM) is a composite of airborne particulate matter collected in St. Louis, Mo. The homogenized bulk material is certified according to its elemental composition for a number of species ranging from the single ppm—to—percent levels. Critical in the evaluation of the analytical performance of the PB-GD systems is the fact that the suggested analysis protocol for SRM 1648 states that 100 milligram samplings of the material should be used in preparation of standard solutions to ensure representative sampling. Less than one (1) milligram samples of the solid material (with average particle sizes less than ten micrometers (10 $\mu$m) are used in the calibration exercises here, leading to a determinate error in the process. Caffeine was used as a test compound to assess the ability of the PB-GDMS to produce molecular mass spectra from organic compounds. The caffeine powder (Aldrich, Milwaukee, Wis.) was stored at 85° C. and ground with a mortar and pestle prior to weighing. For the studies described here, discrete amounts of the SRM and caffeine samples were weighed into an aluminum pan using the balance of a Du Pont (Wilmington, Del.) Model 951 thermogravimetric analyzer and then transferred into a one half (2) dram vial. This particular apparatus is rated with a "1% (of full scale) accuracy in the 10 $\mu$g sensitivity range.

Procedures—For each of the studies described here, the respective PB-GD apparatuses were operated in a continuous fashion, with the plasmas allowed to stabilize prior to beginning an analytical run. Powder samples were introduced by simply holding the sample vials under the end of the stainless steel sniffer 31. The vial was moved around the end of sniffer 31 to vacuum the material into the interface until no particles were observed in the vial. Clearly, this approach adds errors associated with non-quantitative sample introduction.

Figure 9:
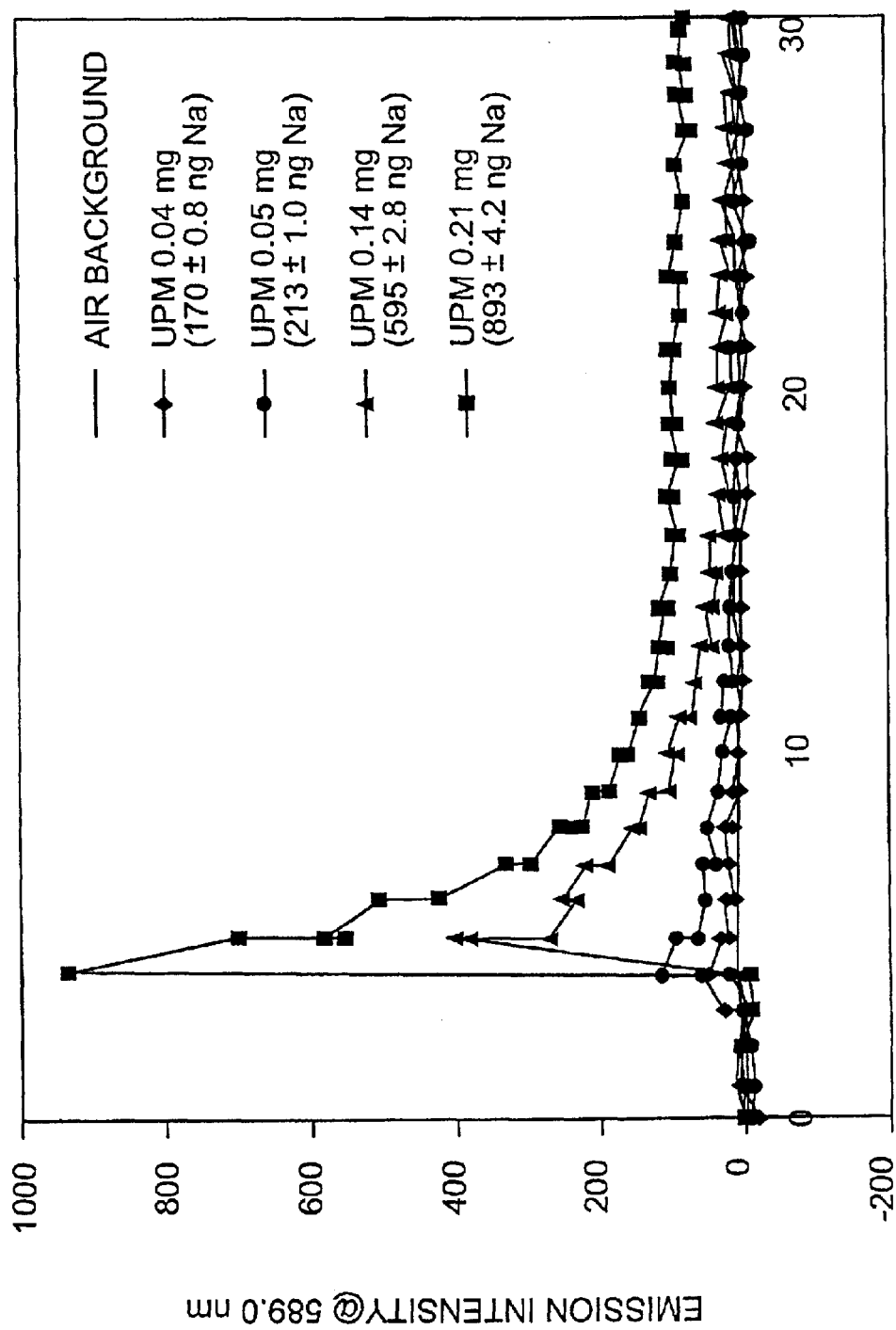
FIG. 9 illustrates Na (I) 589.0 nm atomic emission transients for direct powder introduction of different masses of NIST SRM 1648 Urban Particulate Matter ([Na]=0.425% w:w), discharge current=30 mA, He discharge gas pressure=5 Torr, block temperature=220° C.

FIG. 9 depicts typical atomic emission transients for the Na (I) 589.0 nanometer transition resulting from the introduction of different mass portions of NIST SRM 1648 ([Na]=0.425% w:w). The temporal responses each show the level of spectral background prior to sample introduction, an impulse at the onset of particle introduction, and a slow decay to the baseline level. In practice, the vacuum introduction process is completed in approximately 2 to 3 seconds, so there is some finite residence time for the analyte species within the 5 Torr helium (He) plasma environment. By the same token, it is clear that differences in the time frame over which the discrete samples are introduced may lead to substantive variations in the observed signal-to-noise (S/N) characteristics of the transients. Such variability will affect the computed integrated signal areas and ultimately the quantization quality of the method. Therefore, the system can be improved by the implementation of sample introduction strategies for collected specimens that are more quantitative.

RESULTS AND DISCUSSION

The basic approach at this point in development of the particle beam-glow discharge sampling/analysis methodology has been to establish the basic concept as a potential means of chemical analysis of collected and airborne particulate matter. As described previously, particle beam devices are well known in the aerosol sampling community. However, it is believed that unique to the approach of the present invention is the direct injection of particles into low pressure glow discharges. Successful implementation would present advantages in terms of cost, size, and complexity relative to more established methods of batch particle analysis. Analytical versatility is demonstrated in the present invention through the use of atomic emission (AES) and mass spectrometric (MS) detection. In the case of AES, the advantages of the present invention would include small instrument footprint, simple and inexpensive hardware, simultaneous multi-element analysis, and the ability to generate empirical formulae of organic particle components. The latter quality is based on the fact that "gaseous" elements such as carbon, hydrogen, and nitrogen are viable analytes in this system due to the efficient removal of background gases in the PB interface (31).

Embodiments of the present invention configured for mass spectrometric sampling obviously increase the cost, complexity, and size aspects of the instrumentation. On the other hand, mass spectrometric detection offers the possibility of direct molecular species identification and isotopic distribution information of "elemental" components. The power of mass spectrometry for single particle analysis has been clearly demonstrated in the literature. Described in the following sections are preliminary evaluations of the important plasma parameters which produce analytically useful AES and MS information. First-principle demonstrations of quantification of species present in NIST SRM 1648 are also presented.

Figure 10:
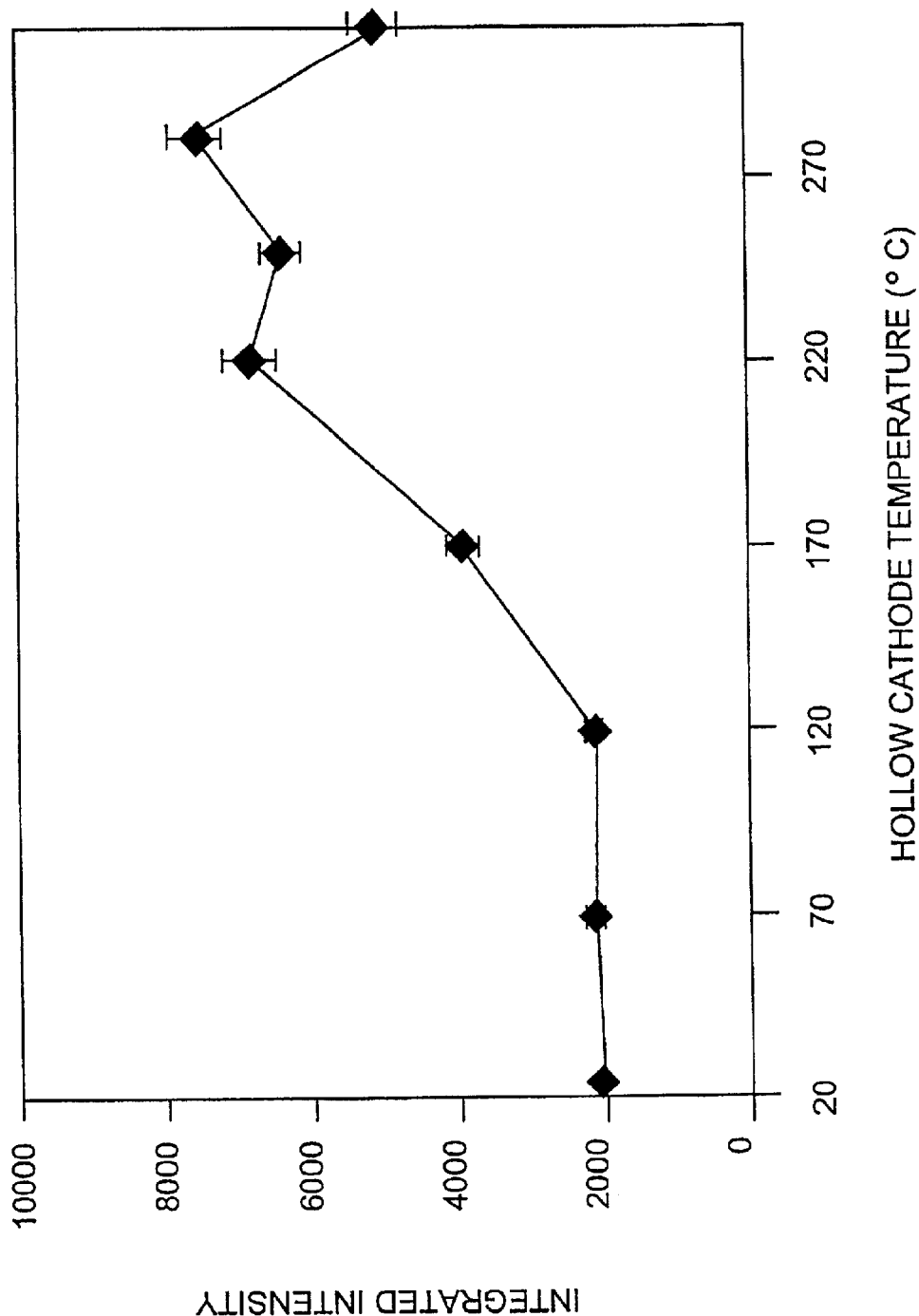
FIG. 10 illustrates the effect of hollow cathode wall temperature on the response of Fe (I) 385.9 nm emission intensity with triplicate introduction of 0.30 mg samples of NIST SRM 1648 Urban Particulate Matter ([Fe]=3.91% w:w), discharge current=40 mA, He discharge gas pressure=2 Torr.

Atomic Emission Detection—Atomic emission analysis of introduced particulate matter is the result of a set of cumulative processes involving vaporization at the heated walls of the hollow cathode, dissociation of 'molecular' species, and collisions with low energy electrons to produce excited state species. The relevant control parameters, therefore, are the wall temperature (vaporization and atomization) and the discharge pressure and current (atomization and excitation). FIG. 10 depicts the response of Fe (I) emission (3.91% w:w in NIST SRM 1648) to differences in the temperature of the wall of thermoblock 44. Triplicate introductions of 0.31 milligram samples of the UPM were performed at each of the indicated temperatures. Clearly seen is the existence of a threshold temperature for effective vaporization. At the three lowest temperature settings, Fe (I) signal is observed, though the mechanism of producing free Fe species is most likely due to cathodic sputtering from the cathode walls. Sputter atomization of particles collected on metallic supports was demonstrated by Van Grieken and colleagues (27) for subsequent analysis by GDMS, as described previously. The amount of vaporized material is seen to continuously increase (approximately three times) as the temperature increases up to 220° C. The Fe (I) response remains relatively constant with further increases in wall temperature, though a roll-over is observed at the highest temperature (310° C.). The decrease in integrated intensity is most likely the result of melting of the PTFE insulator 77 which appeared to partially block the aperture 40d in the side of the hollow cathode 43, causing a decrease in the amount of the UPM entering the discharge region 47. Alternatively, pyrolysis of analyte particles could explain this phenomenon.

Discharge current and pressure are two of the three primary controlling parameters in the performance of any glow discharge source, the third of which is the applied potential (35). In practice, the three parameters are interdependent. In the experiments performed here, the voltage was left as the dependent variable, and the pressure and current were operated at fixed values during a given analysis. The interdependence of the discharge conditions results in differences in the atomization/excitation characteristics in all glow discharge sources, particularly hollow cathodes (36). To a first approximation, discharge current affects the discharge gas ion flux to the surface (i.e., sputtering events) and the density of the electrons in the gas phase (i.e., excitation events). Discharge pressure affects the energy of ions impinging on the cathode surface (an inverse relationship) and the collision frequency and residence time of species within the gas phase. Based on the fact that particle vaporization is controlled by the cathode wall temperature, changes in discharge conditions here would be manifest in differences in the efficiencies of the gas phase processes, which are atomization/dissociation and excitation.

Figure 11:
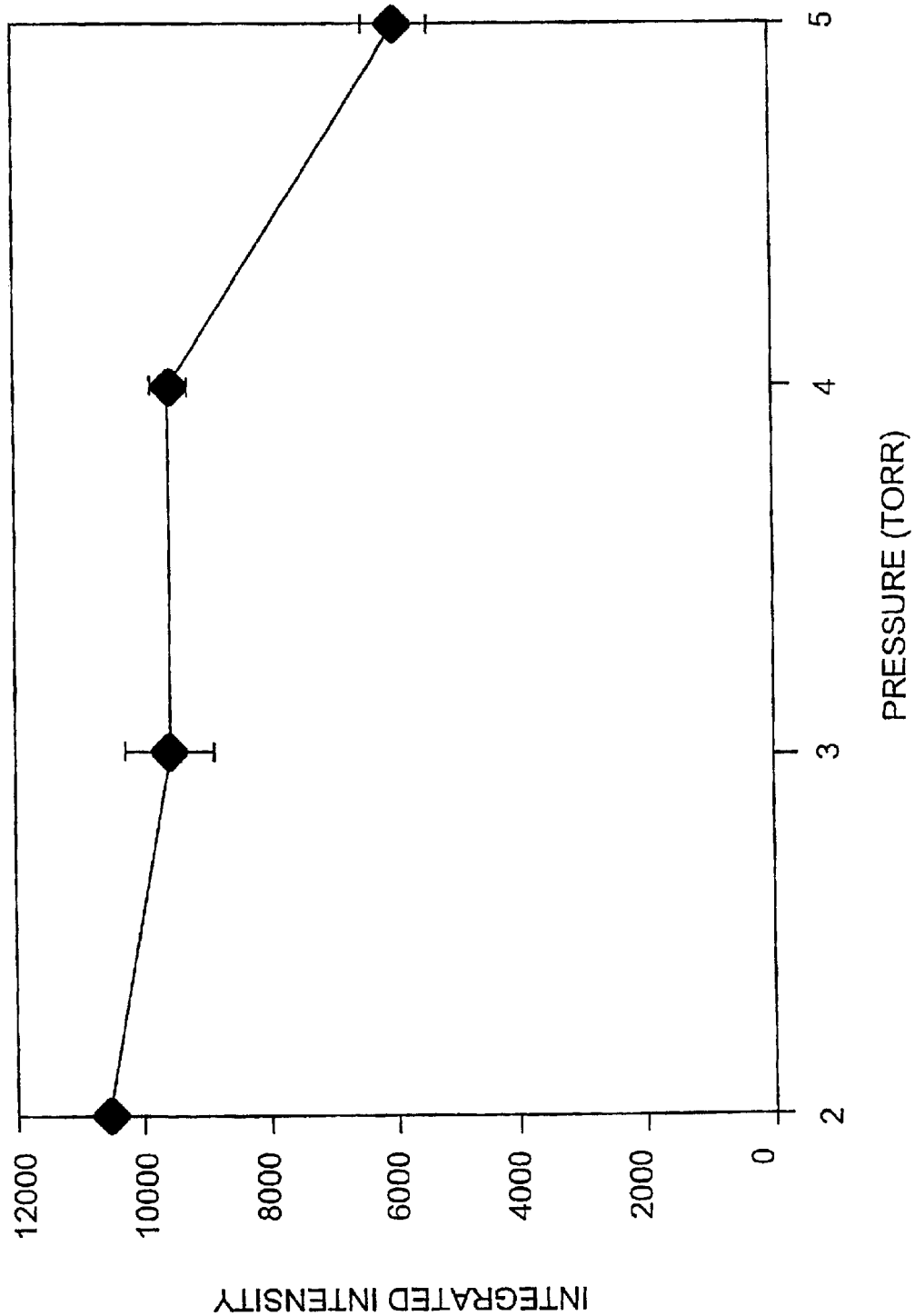
FIG. 11 illustrates the effect of He discharge gas pressure on the response of Fe (I) 385.9 nm emission intensity with triplicate introduction of 0.31 mg samples of NIST SRM 1648 Urban Particulate Matter ([Fe]=3.91% w:w), discharge current=40 mA, block temperature=220° C.

FIG. 11 depicts the response of the Fe (I) 385.9 nanometers emission intensity to differences in the helium discharge gas pressure for a fixed discharge current of 40 milliamperes. Seen here is a typical response for hollow cathode devices, wherein low pressures provide a more energetic excitation environment relative to higher pressures. In this series, the corresponding discharge voltage is decreasing, resulting in lower electron energies within the plasma's excitation volume (negative glow). Somewhat surprising is the fact that increases in pressure do not result in increased residence times of the analyte elements, as might be expected given the shorter mean-free-paths. To the contrary, higher gas flow rates decrease residence times.

Figure 12:
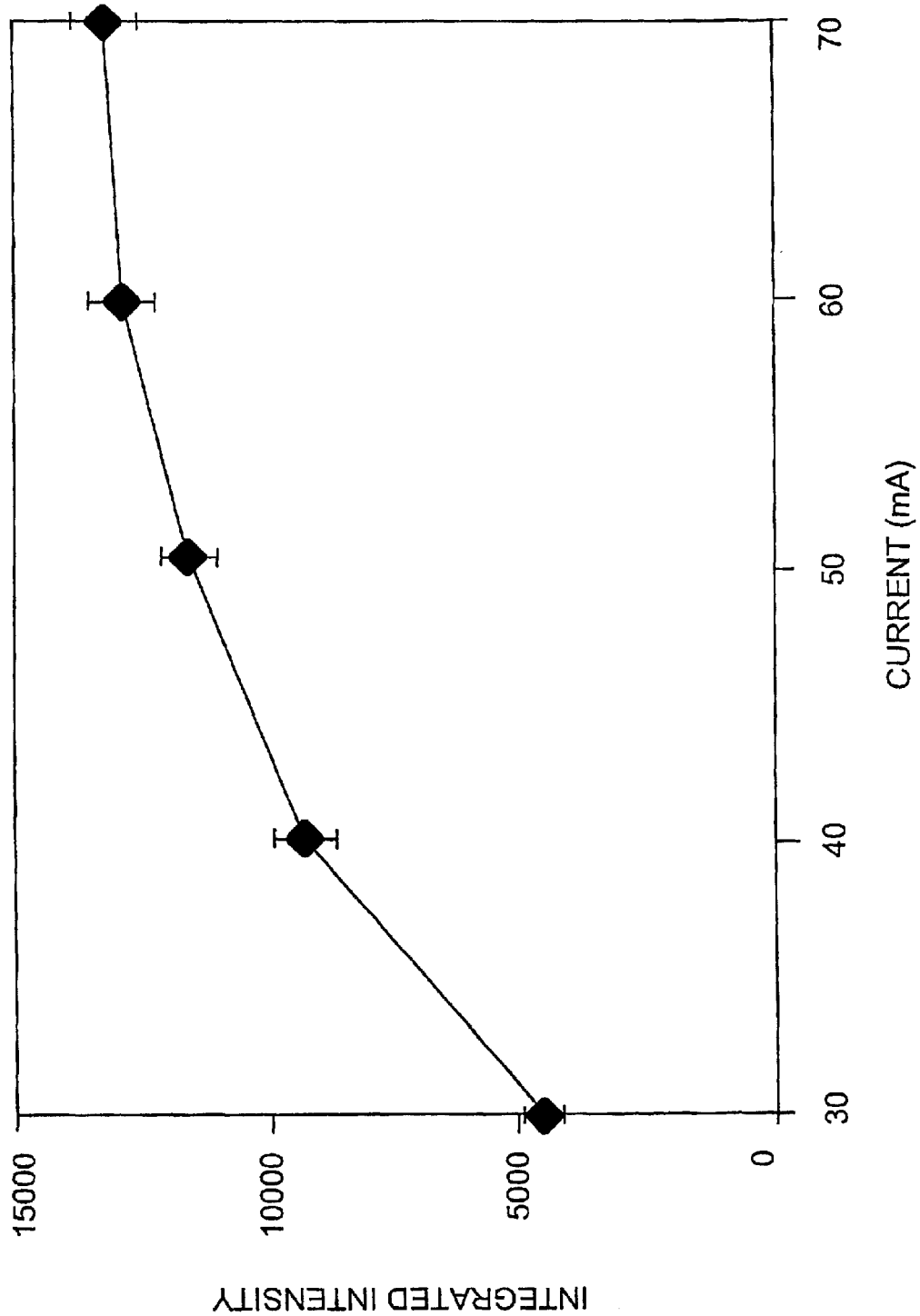
FIG. 12 illustrates the effect of discharge current on the response of Fe (I) 385.9 nm emission intensity with triplicate introduction of 0.26 mg samples of NIST SRM 1648 Urban Particulate Matter ([Fe]=3.91% w:w), He discharge pressure=2 Torr, block temperature=220° C.

FIG. 12 illustrates the response of the Fe (I) 385.9 nanometer emission intensity to changes in discharge current at the fixed discharge pressure of 2 Torr, helium. Clearly seen are the results of enhanced collisional processes within the negative glow of the plasma as the current is increased over a range of from 30 to 60 milliamperes. As in the case of discharge pressure, this is a more-or-less typical response, though the leveling of the responses above 60 milliamperes indicates some form of limiting condition, either in the number of electrons or the analyte mass.

Throughout the course of the discharge parameter evaluation, it was quite typical to observe less than 15% root square deviation (RSD) variation among the triplicate samplings of the UPM. Given the approximately 10% accuracies in the weighing process and the very crude vacuuming of the sample vial, this level of precision is quite encouraging. In addition, the sub-milligram samples used here are three orders of magnitude below those recommended by NIST to achieve acceptable statistics. Therefore, it is felt that the general PB-HC-AES approach to particle analysis shows promise for quantitative analysis.

Figure 13A:
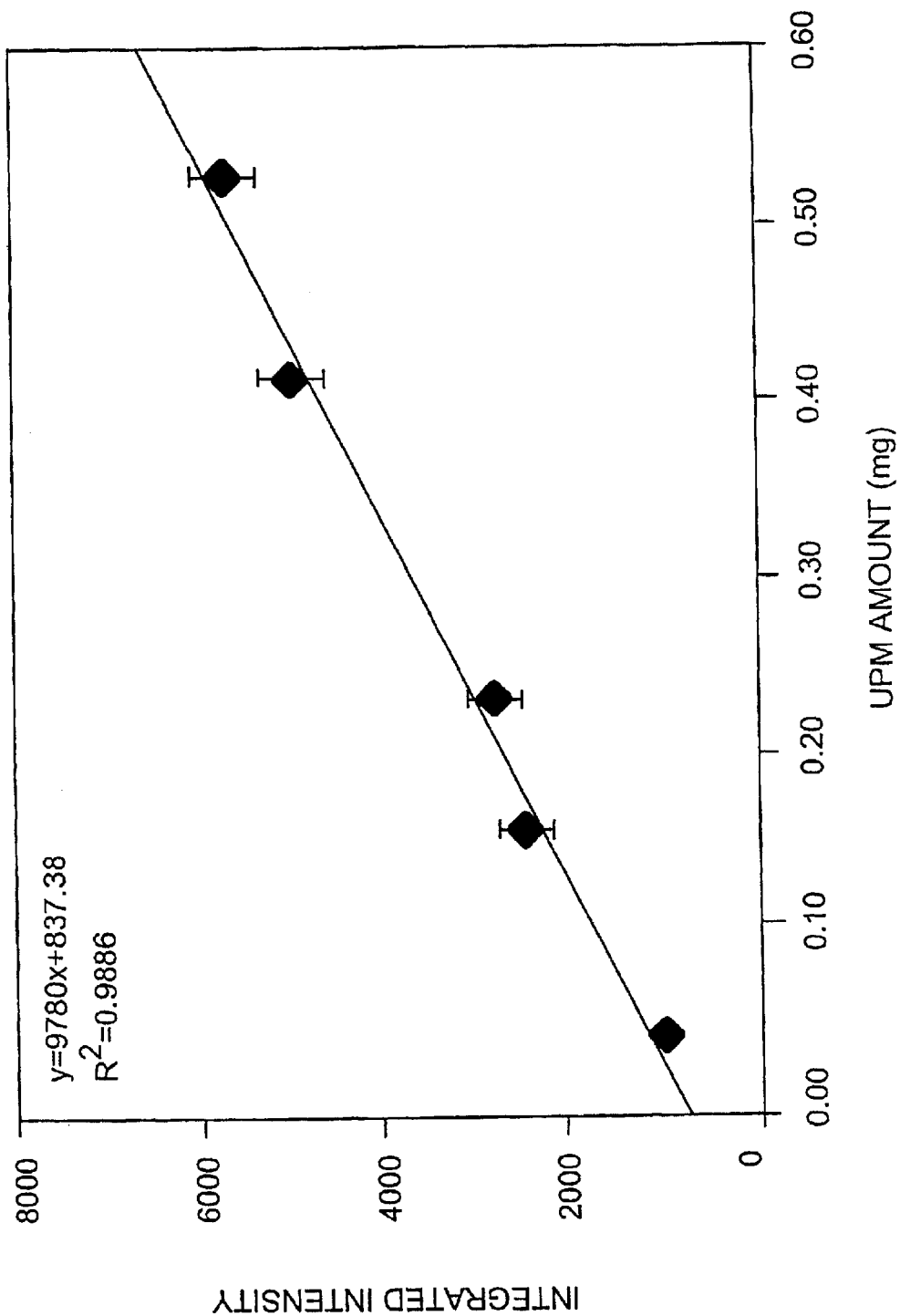
FIG. 13A illustrates the analytical response curve for Fe in NIST SRM 1648, Urban Particulate Matter with monitored wavelength: Fe (I) 385.9 nm, He discharge pressure=2 Torr, discharge current=40 mA, block temperature=220° C.
Figure 13B:
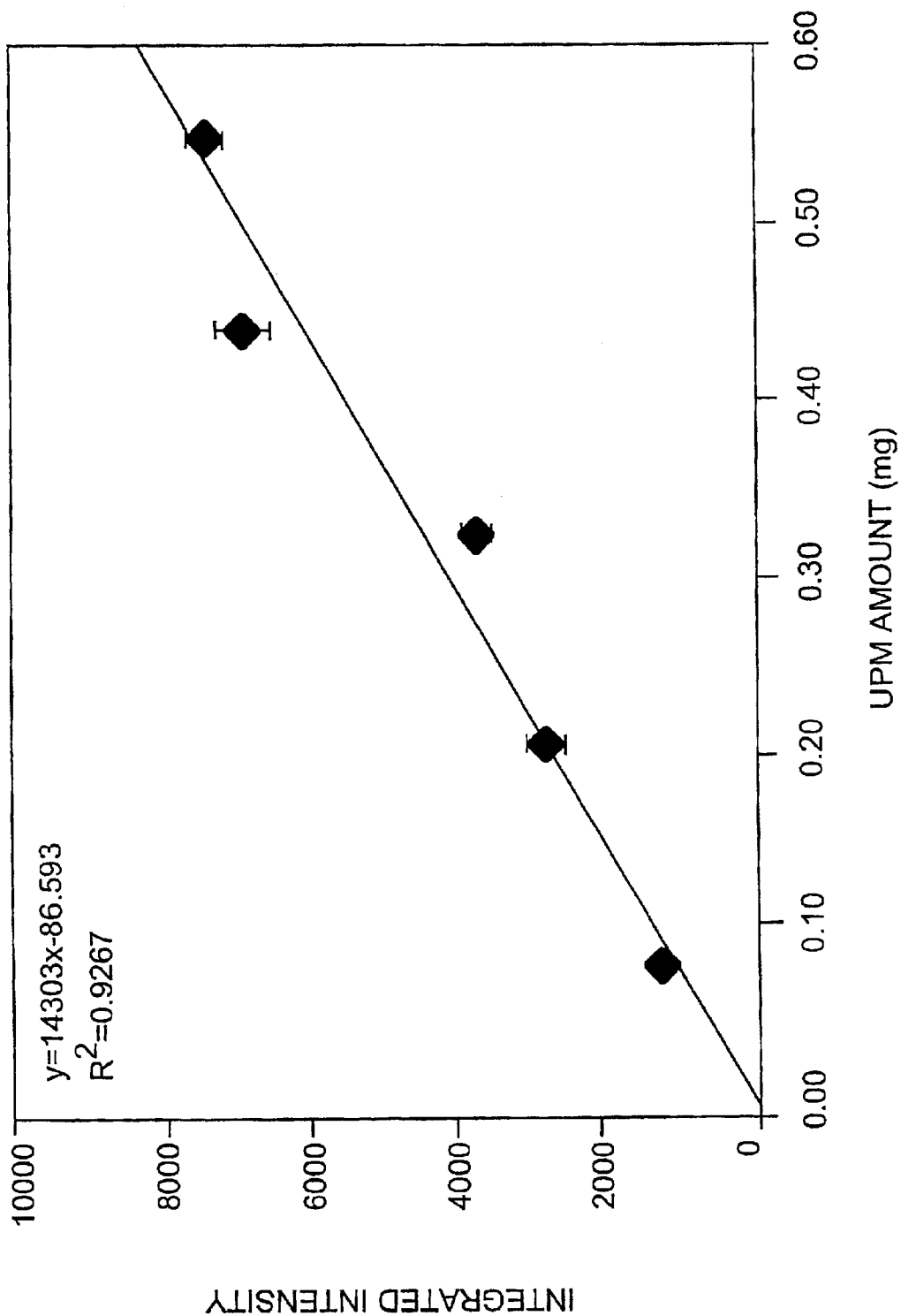
FIG. 13B illustrates the analytical response curve for Na constituents in NIST SRM 1648, Urban Particulate Matter with monitored wavelength: Na (I) 589.0 nm, He discharge pressure=2 Torr, discharge current=40 mA, block temperature=220° C.

FIG. 13A depicts the observed analytical response of Fe (I) 385.9 nanometers. FIG. 13B depicts the observed analytical response of Na (I) 589.0 nanometers emission intensities for the introduction of differing amounts of the NIST UPM. The certified concentrations of these two analytes are 3.91+/−0.1% and 0.425+/−002% w:w, respectively. As can be seen, the responses of both elements are fairly well behaved with respect to a linear calibration function, with the spread in values for triplicate samplings falling well within 15% relative standard deviation (RSD). Limits of detection (LOD) computed using LOD=3 $\delta_{bckgnd}$/slope, yield mass values of 7 and 6 micrograms ($\mu$g) of the UPM for the Fe and Na respectively, which equate to 200 nanograms and 30 nanograms of the respective elements. Given the low level of sophistication at this stage of development, the results seen here are quite encouraging and suggest that further evaluation is certainly in order.

Mass Spectrometry Detection B While the above presentation of the use of the PB-HC-AES for particle analysis demonstrates the basic principles of the sampling approach into the low pressure plasma, the use of mass spectrometric detection illustrates the richness of information that can be obtained. In mass spectrometry, molecular species identification is possible so long as total dissociation is not induced within the ionization source. This is of course the case for high temperature sources such as the ICP, whereas the previously described photoionization (i.e., laser ionization) of single particles produces various fractions of $M^{+\cdot}$ and fragments in the molecular spectra.

Figure 14:
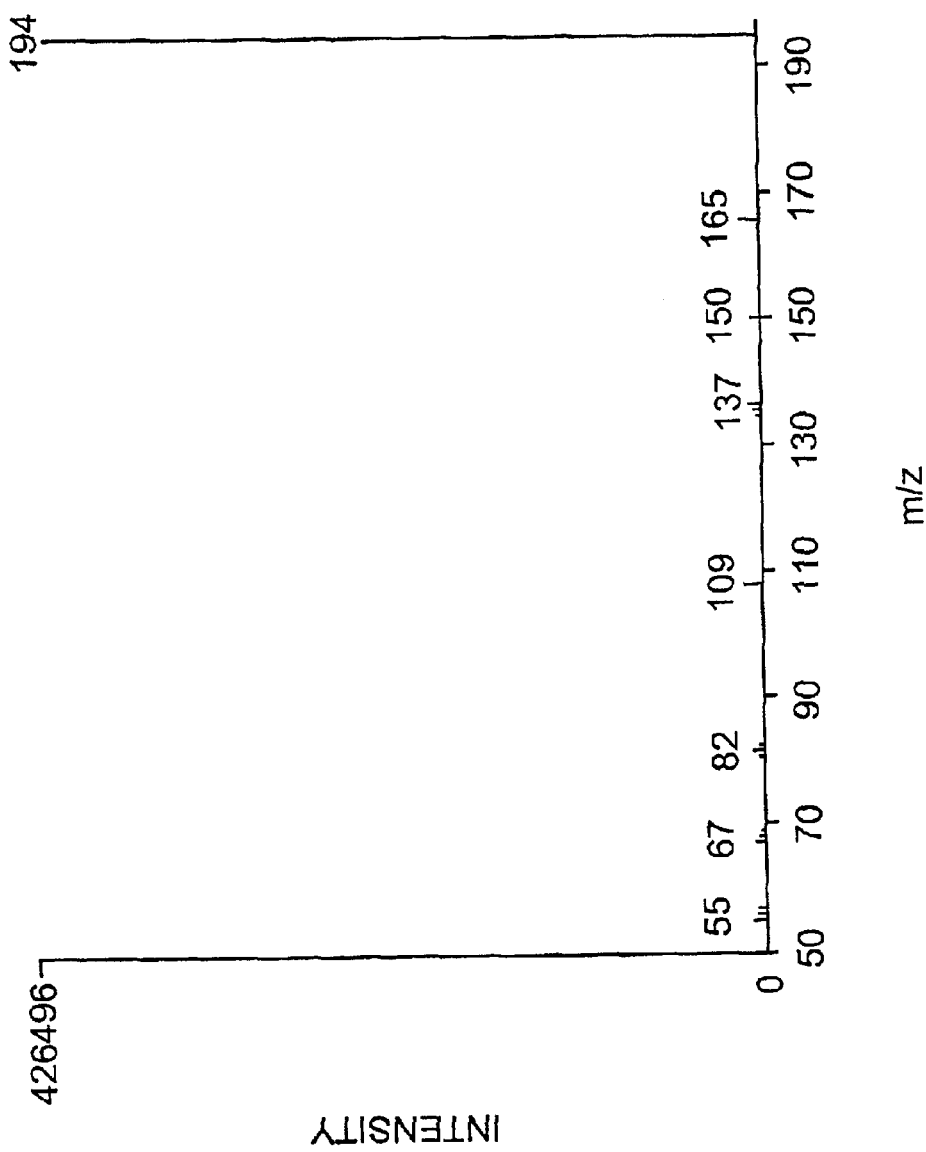
FIG. 14 illustrates the particle beam-glow discharge mass spectrum of a 0.7 mg sample of caffeine powder with Ar discharge pressure=610 mTorr, discharge current=2.0 mA, block temperature=200° C.

FIG. 14 depicts a typical glow discharge mass spectrum obtained for the introduction of 0.7 milligrams of caffeine particles through the PB interface. As can be seen, the spectrum is dominated by the molecular ion ($M^+$.) at m/z=194, with characteristic fragments appearing at m/z=165, 150, 137, 109, 82, 67, and 55 amu. The extent of fragmentation is very similar to that produced in classical electron impact (EI) sources. The low degree of fragmentation in this spectrum demonstrates a number of key attributes of the PB-GDMS approach. First, the vaporization of the particles at the cell wall does not induce appreciable pyrolysis. Second, the gas phase temperature within the discharge is sufficiently low such that extensive dissociation does not occur. Third, the ionization within the glow discharge is energetically similar to EI sources. While much more extensive characterization is required, the promise of library searchable product mass spectra greatly enhances the potential utility of this approach to particle analysis.

As in the case for the particle beam-hollow cathode-atomic emission spectrometry (PB-HC-AES) studies, the roles of vaporization temperature, discharge current, and source operating pressure were evaluated for the mass spectrometric detection system. The effects of these parameters on the mass spectrometric source performance are expected to be different than for the cathode-atomic emission spectrometry source, where the hollow cathode forms an integrated vaporization and excitation volume. In the mass spectrometric source used to generate the data presented herein, the discharge volume 87 (FIG. 7) is indeed a hollow cylinder, but the negative glow is centered at the surface of a planar cathode 79 mounted on the direct insertion probe 61. Therefore, vaporized material must be transported (diffuse) into the glow discharge plasma region.

Figure 15:
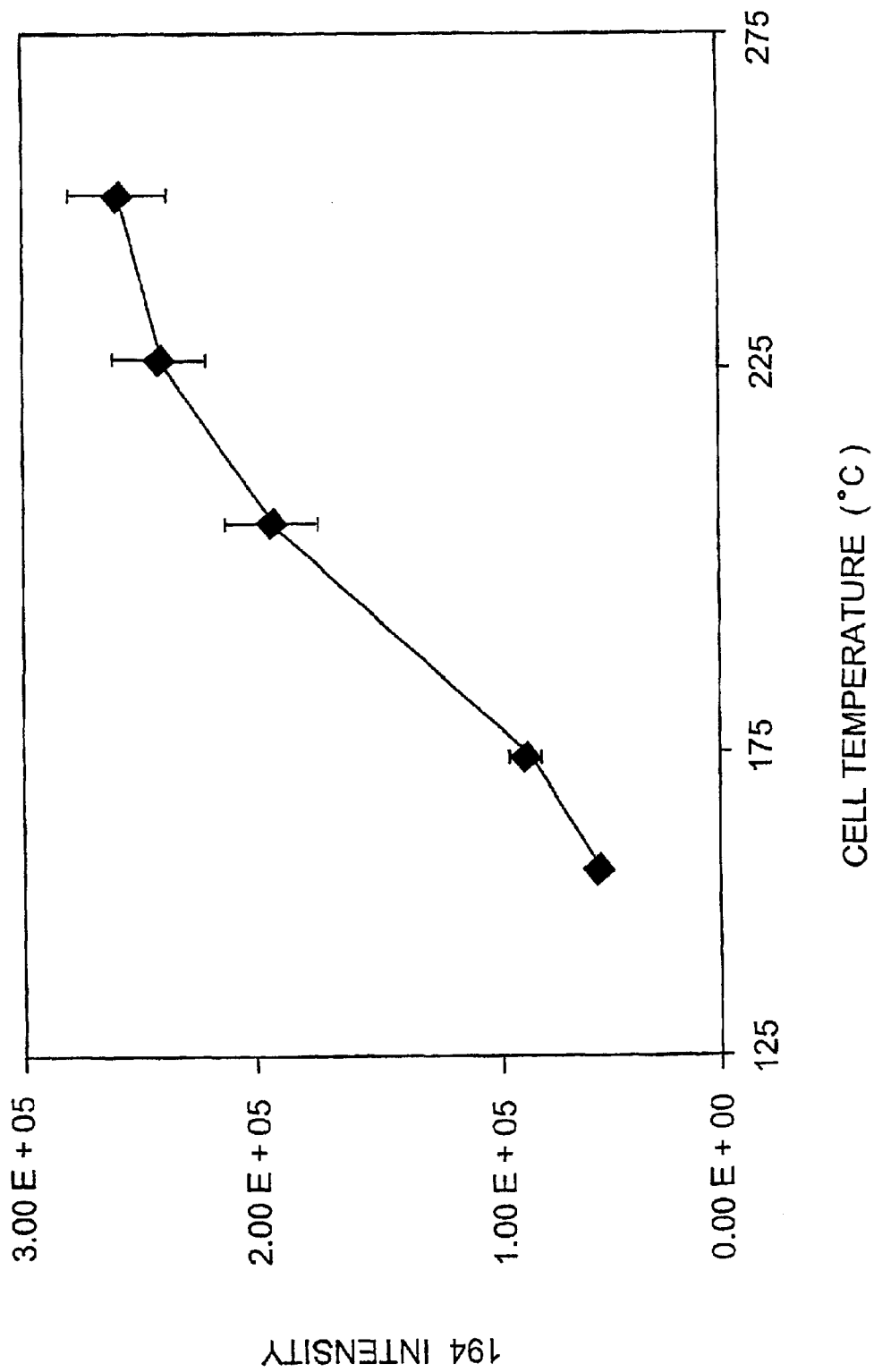
FIG. 15 illustrates the effect of block (wall) temperature on the response of the caffeine molecular ion (m/z=194 amu) with triplicate introduction of 0.7 milligram samples, discharge current=1.0 milliampere, Argon discharge gas pressure=610 milliTorr.

FIG. 15 depicts the response of the m/z=194 molecular ion ($M^+$.) signal derived from 0.7 milligram amounts of caffeine particles as a function of the cell wall temperature. The response here is very similar to that seen in FIG. 10 for the PB-HC-AES system as a vaporization threshold temperature of approximately 200° C. is quite apparent. In general, the level of precision in the PB-GDMS data are quite similar to the AES data, though the variability of the triplicate introductions increases (up to 13% RSD) in the mass spectrometric case at the higher temperatures. The reason for this loss in precision is explained by the differences in the source geometries, where the relatively cool DIP and cathode act as condensation points within the mass spectrometry source. This explanation is supported in the extension of the mass spectrometric signal transients for introduced UPM (versus AES transients) and is confirmed in the observation of deposition on the probe. Future developments of the PB-GDMS source will include the use of a hollow cathode geometry to address the less efficient vaporization seen here relative to the atomic emission source.

Figure 16:
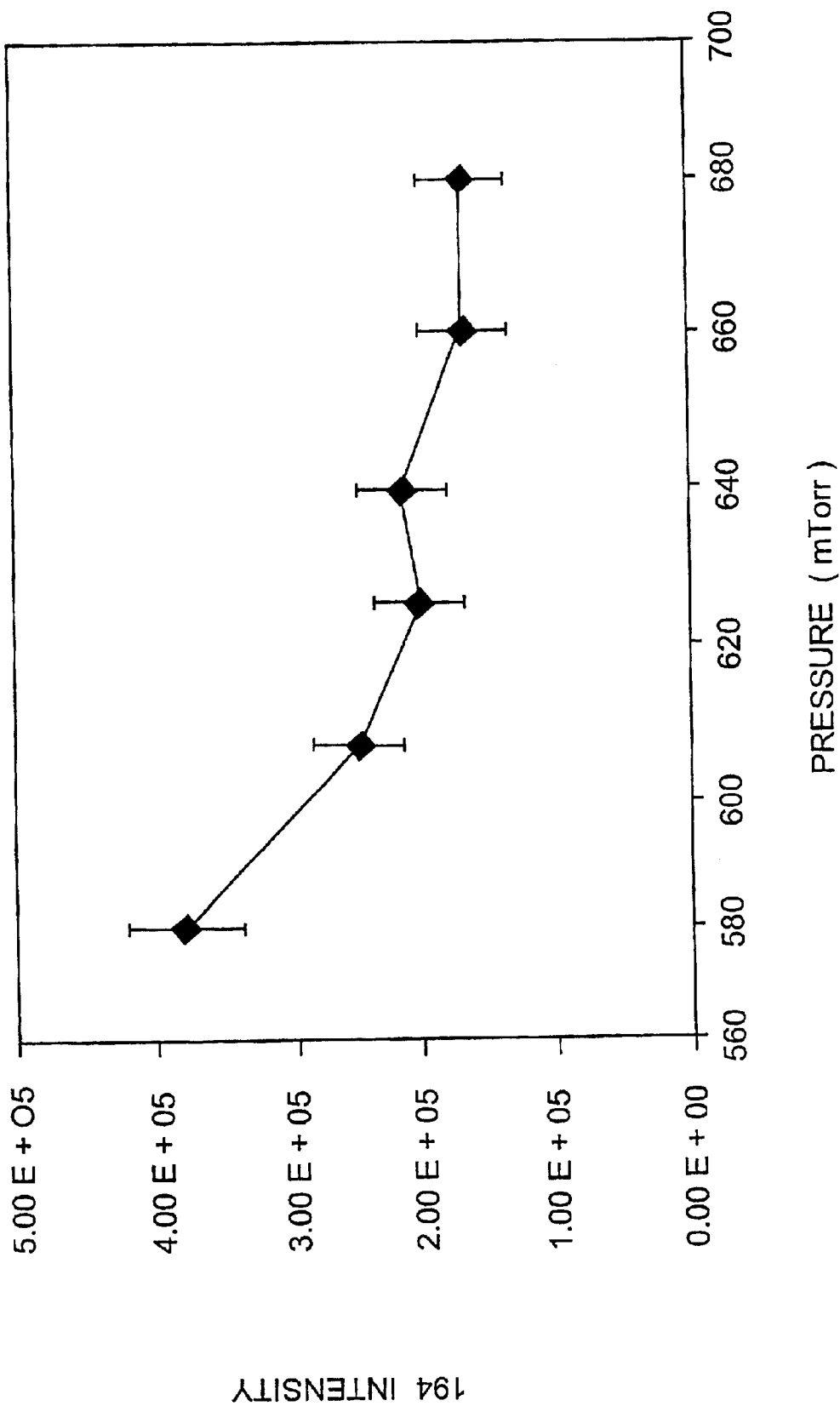
FIG. 16 illustrates the effect of Ar discharge gas pressure on the response of the caffeine molecular ion (m/z=194 amu) intensity with triplicate introduction of 0.7 mg samples, discharge current=1.0 mA, block temperature=200° C.
Figure 17:
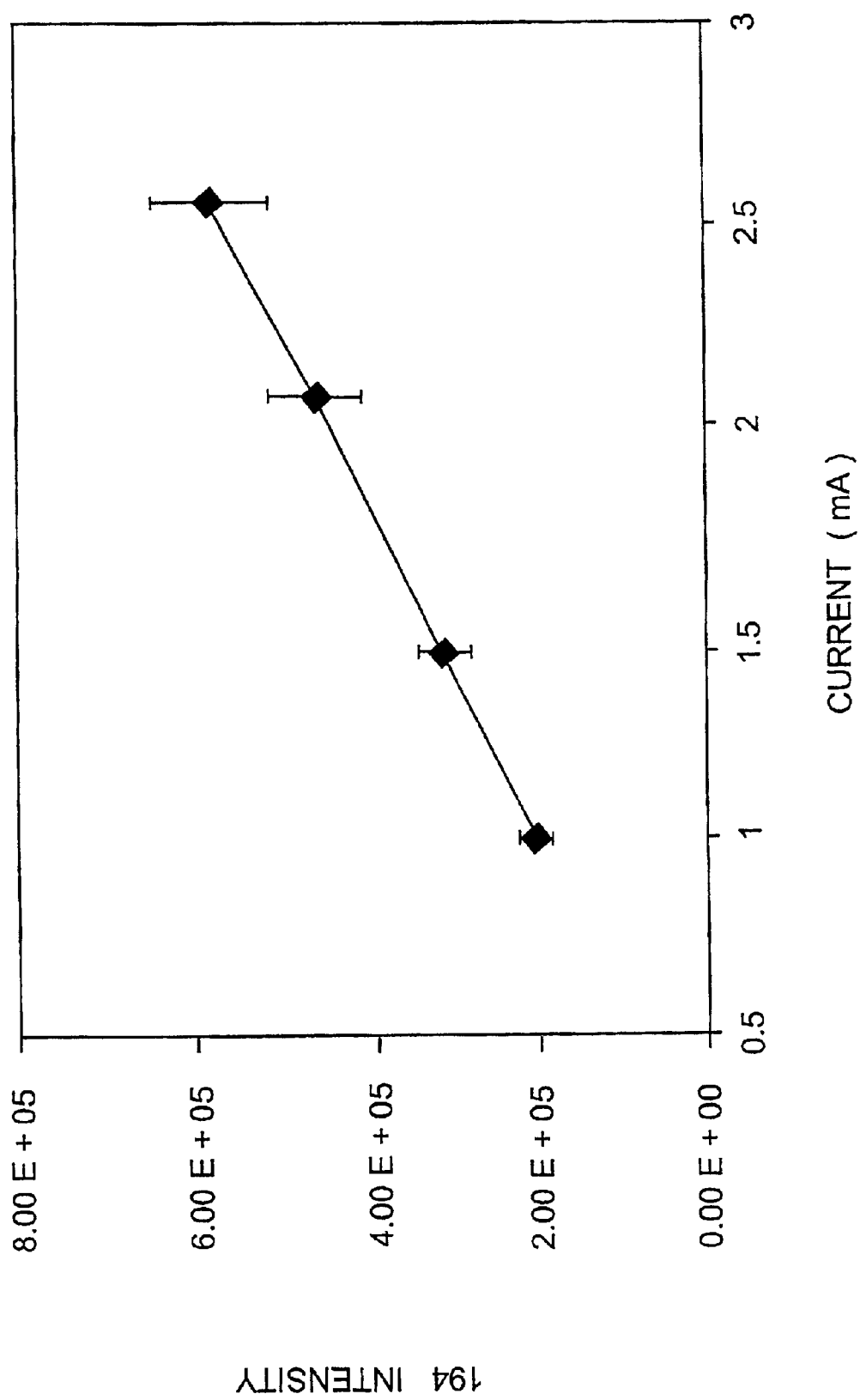
FIG. 17 illustrates the effect of discharge current on the response of the caffeine molecular ion (m/z=194 amu) intensity with triplicate introduction of 0.7 mg samples, Ar discharge gas pressure=610 mTorr, block temperature=200° C.

The respective roles of ion source pressure and discharge current are shown in FIGS. 16 and 17 for introduced caffeine particles. In the case of mass spectrometric detection, ionization of vaporized particulate matter can occur via collisions with plasma electrons and metastable discharge gas species ($Ar_m^*$), termed Penning ionization. Ion source pressure affects both of these populations within the plasma, as well as the collision frequencies and energetics. Thus it would be expected that the character of an organic molecule's mass spectrum might also change with source pressure. In fact, mass spectra acquired at each condition show very little change in the proportion of molecular and fragment ions. As seen in FIG. 16, increases in argon pressure in the discharge source tend to suppress the signal intensity of the m/z=194 caffeine molecular ion. This response could reflect either (or both) a decrease in $Ar_m^*$ densities or lower electron energies, as both are known effects. As would be expected, based on the AES response, increases in discharge current produce proportional increases in molecular ion intensities as shown in FIG. 17. While the higher currents produce higher levels of analyte signal and some improvement in sample-to-sample precision (11 to 8%RSD), the accompanying heating of the probe tip led to fouling of the cathode over extended periods of time.

Figure 18:
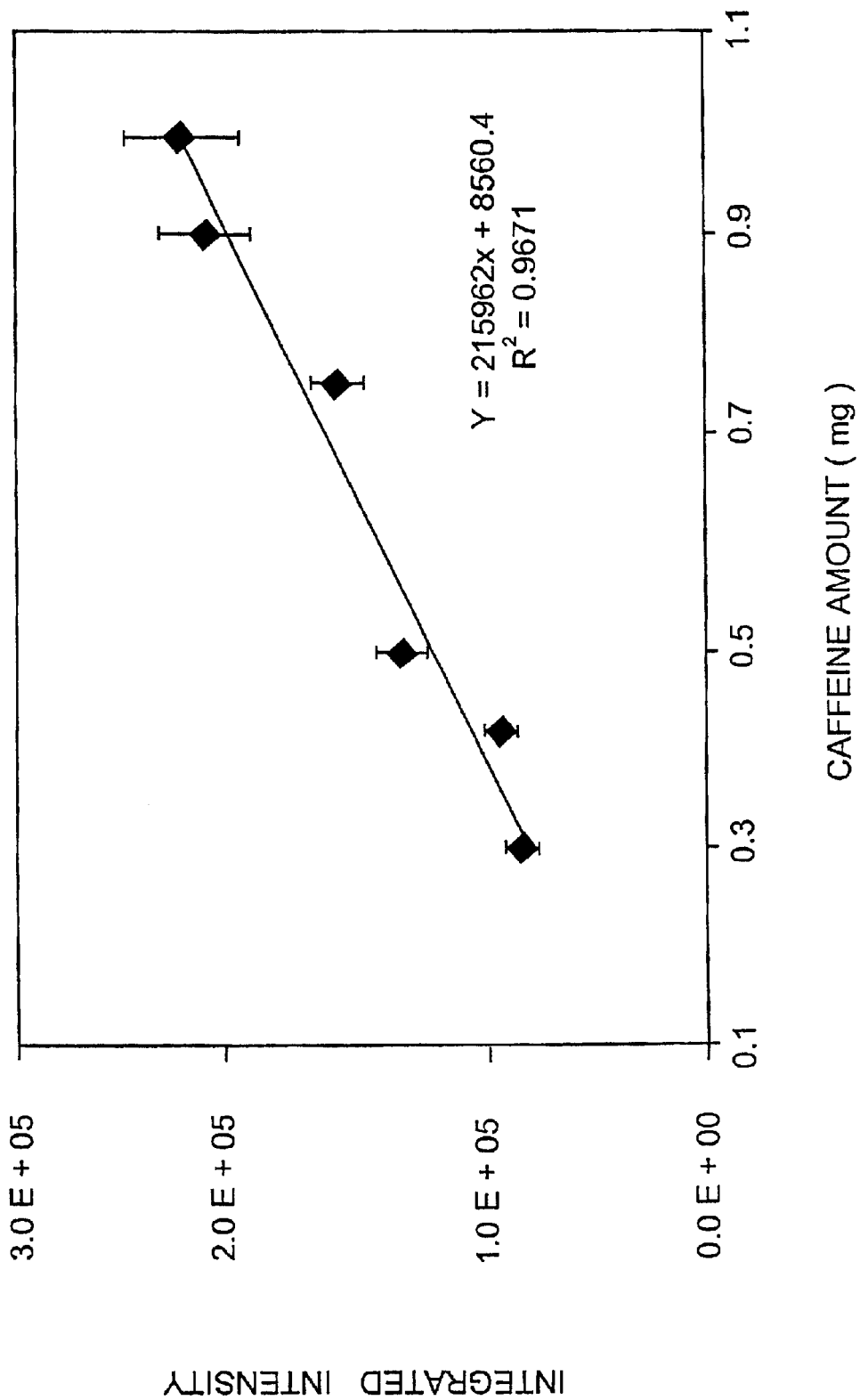
FIG. 18 illustrates the analytical response curve of the total GDMS ion signal of caffeine (e.g., molecular ion and fragments) with discharge current=1.0 mA, Ar discharge gas pressure=610 mTorr, block temperature=200° C.

Compromise discharge conditions of 200° C. wall temperature, 610 milliTorr argon source pressure, and a discharge current of one (1) milliampere (mA) were expected to produce plasmas of sufficient stability to perform a simple investigation of the quantification characteristics of the PB-GDMS approach to particle analysis. FIG. 18 depicts the analytical response of the total product ion signals (i.e., $M^{+\cdot}$ and fragments) for various masses of introduced caffeine powder. As can be seen, there is a reasonably good correlation between introduced particle mass and ion signal intensity. In addition to weighing errors and non-quantitative sampling, the 0.25 scans/sec quadrupole analyzer scan rate also contributes to the non-ideal (9% RSD) response. Integration of the background signal levels prior to the triplicate injection of the lowest sample mass provides a basis for computing a limit of detection of 284 nanograms of caffeine. It is believed that there is much room for improvement through better sampling and reconfiguration of the ion source geometry to a hollow cathode configuration as used in the AES studies here.

Figure 19:
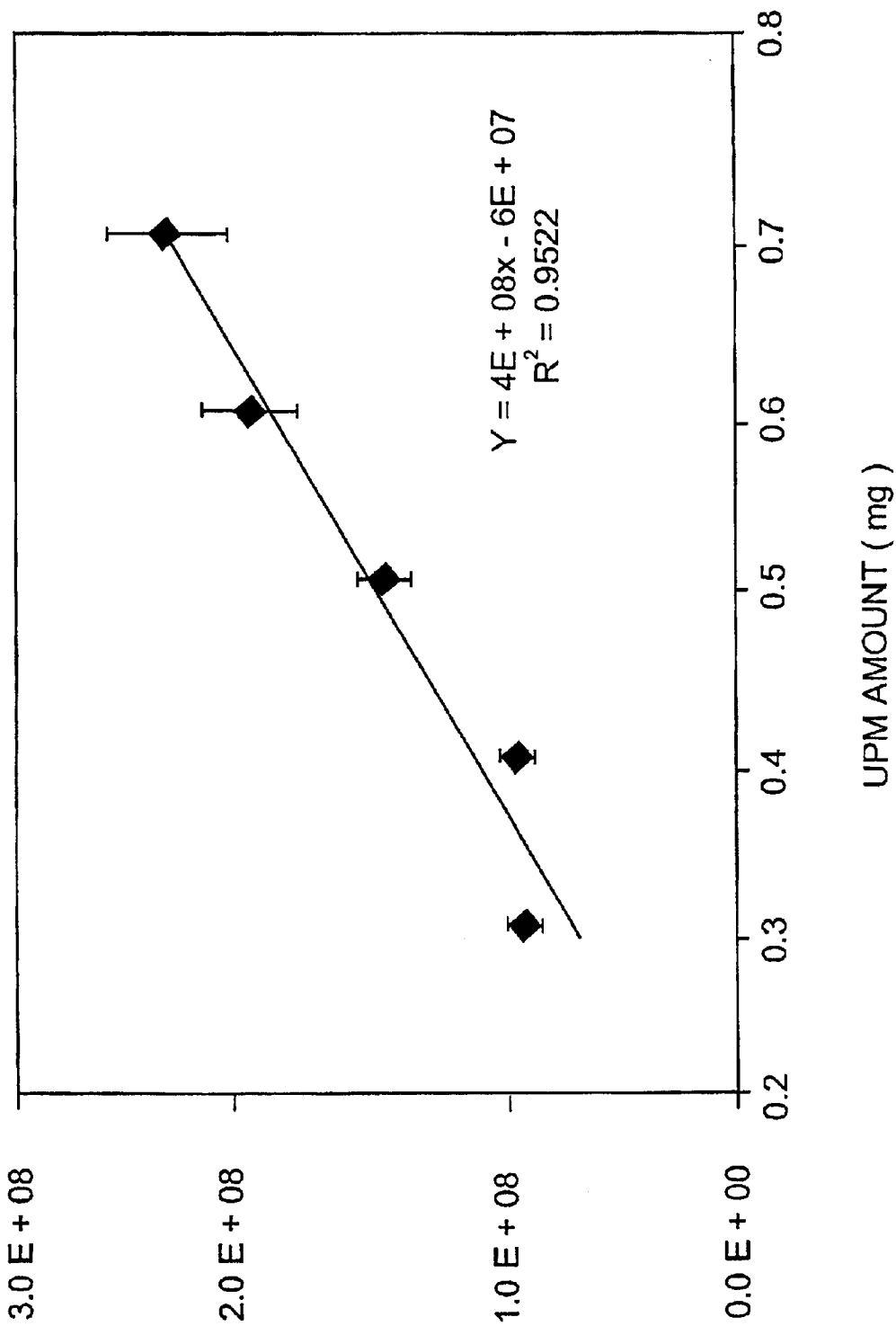
FIG. 19 illustrates the analytical response curve for $^{56}Fe^+$ in NIST SRM 1648, Urban Particulate Matter ([Fe]=3.91% w:w) with Ar discharge pressure=610 mTorr, discharge current=1.0 mA, block temperature=200° C.

To complement the data obtained for the introduction of pure organic particles, FIG. 19 represents the analytical PB-GDMS response of the $^{56}Fe^+$ isotope obtained for different masses of the NIST Urban Particulate Matter. It must be emphasized that the same discharge conditions employed in the analysis of caffeine particles has been employed in this evaluation. Single ion monitoring (SIM) was employed to capture the respective signal transients and compute integrated signal intensities. As can be seen, the analytical responses are proportional to the mass of the introduced powder samples, though with a lower degree of correlation than for the caffeine particles. The obtained detection limit is 175 nanograms of the SRM, equivalent to approximately 7 nanograms of the Fe analyte. This PB-GDMS detection limit is approximately a factor of four (4) lower than that obtained in the PB-HC-AES experiments, and most likely can be attributed to the partitioning of Fe (I) emission across thousands of optical transitions vs. 91.7% in the $^{56}Fe$ isotope monitored here.

The fact that the UPM data here were taken at the same discharge conditions as the "molecular" analyte is significant for two reasons. First, it points to an inherent capability to perform global (elemental and molecular) analysis for a given particulate matter sample. Second, it does not rule out the possibility that there may in fact be more optimum discharge conditions if one were solely looking to perform elemental analysis. It could also be imagined that there may be harsher conditions that may effect more complete dissociation of composite species. Future studies will certainly focus on the dual mode capabilities afforded by the GDMS ionization process relative to solely elemental spectra obtained from atmospheric pressure plasmas.

Figure 20:
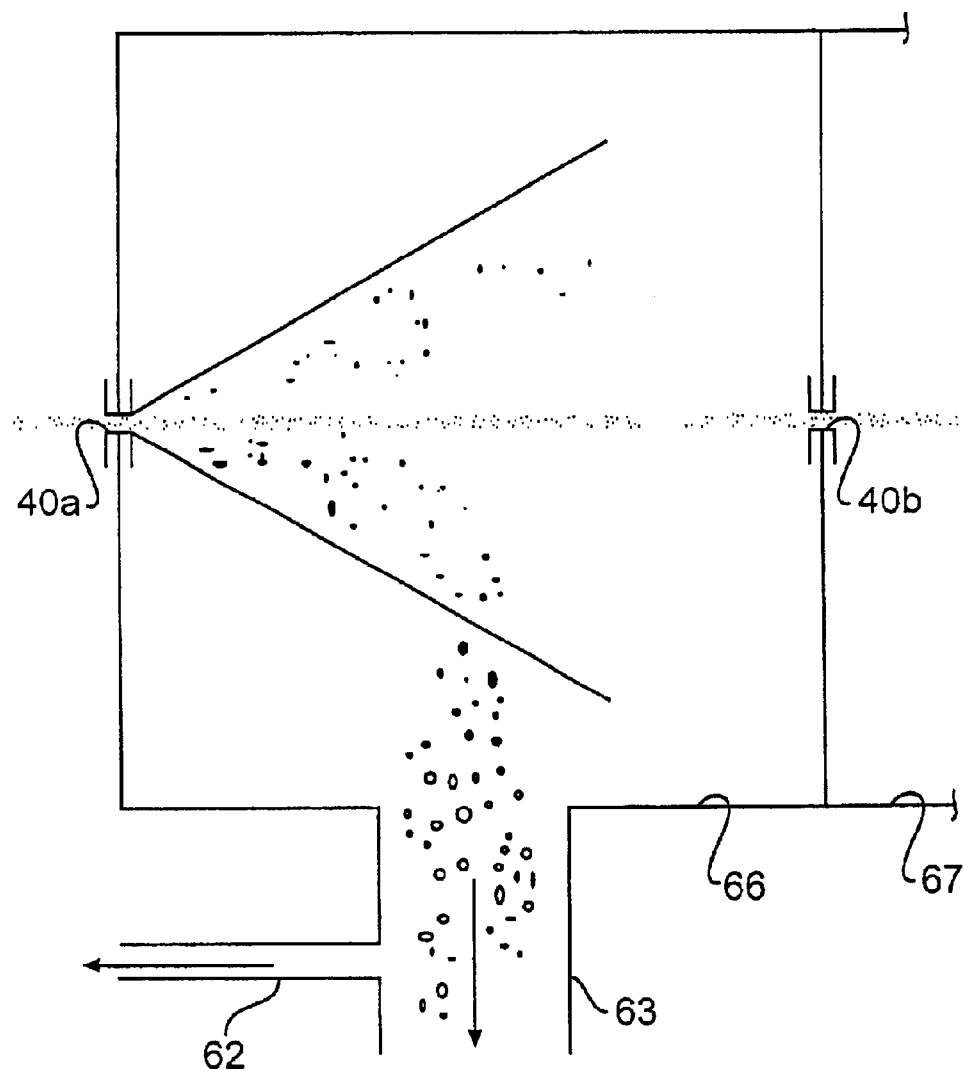
FIG. 20 presents in a diagrammatic view, components of a presently preferred alternative embodiment of the PB-GD apparatus of the present invention configured to analyze the gas that is separated from the particles in the momentum separator.

Alternative embodiments of the invention B An alternative embodiment of the present invention provides information about the gaseous components of the sampled aerosol as well as the particles in the aerosol. In this alternative embodiment, the gas that is separated from the particles in the momentum separator 41, can be analyzed in addition to the particles that pass through the separator 41 and form particle beam 80. As shown schematically in FIG. 20, one way of segregating the gaseous components can be accomplished using an auxiliary bleed line 62 off one of the pipes 63, 63a leading to one of the evacuation pumps 64, 65 of the momentum separator 41. In an alternative approach for segregating the gaseous components that is diagramed in FIG. 21 for example, an auxiliary bleed line 62 is connected in communication with the first chamber 66 of the momentum separator 41 and has its own evacuation pump 85 to remove the gaseous components for separate analysis. Both ways of segregating the gaseous components ultimately can be connected in communication with a second hollow cathode emission source 26a and/or some other analytical instrument.

FIG. 21 is a schematic diagram of an alternative embodiment of the present invention configured to provide chemical analysis of particles via atomic emission spectrometry and mass spectrometry and particle size analysis in beam 80 (FIG. 22) by laser light scattering. Referring to FIG. 21, the representation labeled "Aerosol" represents the source of the particulate matter to be analyzed. This particulate matter is drawn into sniffer 31 by the vacuum action created by the roughing pumps 64, 65 that provide the reduced pressure environment within the momentum separator. A turbo molecular pump 68 is labeled "Turbo 1" and provides the reduced pressure within the thermal block 44 that forms part of the hollow cathode excitation/ionization source 26. This first source 26 emits light through a transparent member 55, and this light emission is indicated by the arrowhead with the wavy tail. The light is measured by an optical detector such as an acousto-optic tunable filter/detector 84 that measures the spectrum of the output light from the emission source 26.

As schematically shown in FIG. 21, the gaseous matter is bled off of the first chamber 66 of the momentum separator and introduced into a second low pressure plasma generator 26a such as a hollow cathode excitation/ionization source. The light emitted from this second hollow cathode excitation/ionization source 26a is also input to an acousto-optic tunable filter/detector. This can be the same detector 84 that receives the input light from the first hollow cathode excitation/ionization source 26. Alternatively, a second acousto-optic tunable filter/detector can be provided to receive the input light from the second hollow cathode excitation/ionization source 26a. The second hollow cathode emission source 26a is used to identify the chemical composition of the gases in which the particulate matter 80a is entrained, while the particulate matter 80a is analyzed simultaneously by the first hollow cathode emission source 26. A separate roughing pump 85 is provided for the second hollow cathode emission source 26a. Each hollow cathode excitation/ionization source 26, 26a is powered by either direct current, microwave or radio frequency power.

As schematically shown in FIGS. 2 and 21, a mass spectrometer 60 such as a quadrupole mass filter receives ionic species via the ion optics 69 that extracts ionic species from the first hollow cathode source 26 via exit aperture 83. As schematically shown in FIG. 21, a second turbo molecular pump (designated "Turbo 2") maintains the mass spectrometer 60 under reduced pressure. The masses of the molecules and atoms constituting the particles are analyzed by a mass spectrometer 60 such as the quadrupole mass filter schematically shown in FIG. 21 (or another type of mass analyzer) that is configured to allow ions with a given mass/charge ratio to reach a detector 81.

Figure 8:
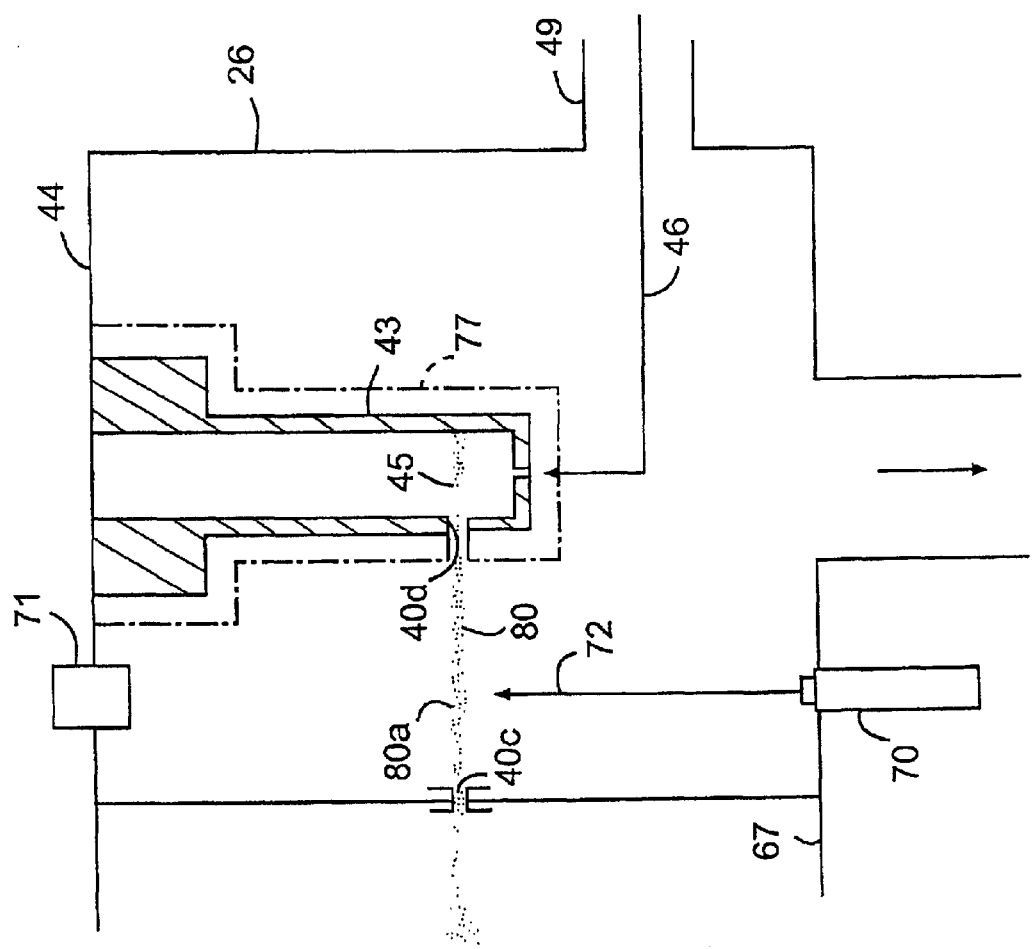
FIG. 8 presents in a diagrammatic view, a presently preferred alternative embodiment of the PB-GD apparatus of the present invention configured to use a low-power laser scattering device to obtain information about the size distribution of the particles.

In other alternative embodiments, such as those schematically shown in FIGS. 2 and 8 for example, it is possible to obtain information about the size distribution of the particles 80a in the particle beam 80 by using an instrument such as a low-power laser scattering device consisting of a low-power laser 70 and a detector 71. This low-power laser scattering device can be disposed to operate on the particle beam 80 before the particle beam enters into the glow discharge unit 26. As shown in FIG. 2 for example, the low power scattering device 70, 71 provides outputs that are monitored by a computer 58. Such monitoring is schematically indicated in FIG. 2 by the connecting lines designated 58c and 58d.

Figure 22:
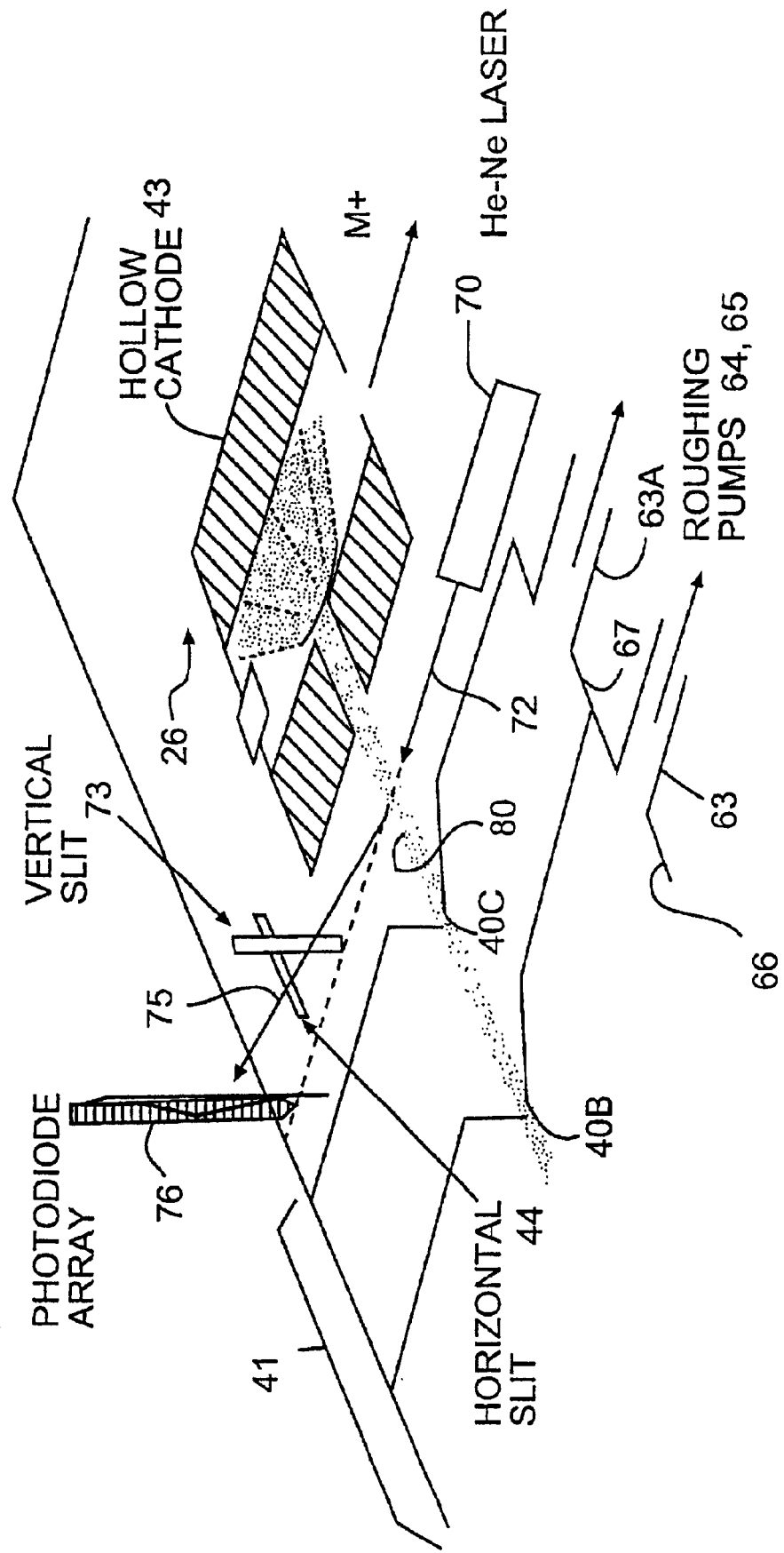
FIG. 22 is an exploded view of a portion of the diagram of FIG. 21 in the vicinity designated by the arrow labeled "scattering region"

FIG. 22 illustrates the region labeled "scattering region" in FIG. 21. In this scattering region, one embodiment of low power scattering device that includes laser 70 and array detector 76, is provided to permit the size of the particles to be determined. The device includes a laser 70 and a detector, which is schematically indicated in FIG. 8 by the rectangle numbered 71. As schematically shown in FIG. 22, a helium/neon laser 70 is oriented to provide a laser beam 72 at an angle that is perpendicular to the direction of the movement of the particulate matter in particle beam 80. Laser 70 is disposed so that its beam 72 intersects particle beam 80 after beam 80 exits the momentum separator 41 and before beam 80 enters the low pressure plasma 26. In an orientation opposed to the laser output beam 72, a vertical slit 73 is provided to collect laser light scattered in a head-on direction from the laser 70. The light passing through the vertical slit 73 is then collected through a horizontal slit 74 that is oriented at a predetermined angle with respect to the initial direction of the laser beam 72 before it is scattered by the particle beam 80. The light passing through the vertical slit 73 and the horizontal slit 74 is schematically represented by the arrow designated with the numeral 75. This light 75 passing through the vertical slit 73 and the horizontal slit 74 is then collected by a detector such as a photo diode array 76. The light detected by array 76 is a function of the size of the particles in the particle beam 80. Thus, detector 71 includes vertical slit 73, horizontal slit 74 and photo diode array 76.

The foregoing is but one possible arrangement for determining the size of the particles that compose the particle beam 80. Other methods of performing the light scattering are possible. One such alternative implementation of a low-power laser scattering device is described in U.S. Pat. No. 5,681,752 to Prather, which is hereby incorporated herein by this reference.

The arrangement illusted in FIGS. 21 and 22 provides real time analysis of the size of the particles in the particle beam as well as the chemical composition of the particles in the particle beam. The information from which the chemical composition is determined is provided by the analysis of the light emitted from the first hollow cathode source 26 and the ionic species extracted from the first hollow cathode source and analyzed by the quadrupole mass filter 60. Additionally, the chemical composition of the gas is analyzed by the light emitted from the second hollow cathode emission source 26a. Time comparison of the analytical data provided by the detector 81 of the quadrupole mass filter 60, the acousto-optic detectors 84, and the laser scattering device 70, 71, can be time-adjusted to determine both the size and chemical composition of the particles composing the particle beam 80 extracted from the environment of the sniffer 31.

Conclusions

The coupling of a particle beam sample introduction interface to low pressure glow discharge plasmas has been shown to be a viable approach to the analysis of particulate matter. Particle introduction to a hollow cathode discharge source for atomic emission spectroscopy detection (PB-HC-AES) provides a relatively straightforward means of performing elemental analysis of samples such as the NIST SRM 1648, Urban Particulate Matter. Because the system employs a vacuum interface to the plasma, both collected and airborne particles are easily sampled. The use of the low power plasma affords a compact, inexpensive platform which could be employed in remote monitoring situations. In addition, the low pressure inert gas plasma permits the analysis of "gaseous" elements such as C, H, and N. Improvements in sample introduction methodology and further optimization of the discharge geometry (specifically the diameter of the hollow cathode 43), are likely to yield lower limits of detection and better precision. Finally, the implementation of simultaneous (e.g., diode array) detection schemes will enhance the utility and practicality of the system.

The coupling of the particle beam interface to a glow discharge mass spectrometer ion source (PB-GDMS) produces a higher level of information content for introduced particles, as both molecular and elemental mass spectra may be obtained under the same discharge conditions. While the present discharge geometry produced suitable performance, future iterations will definitely include a hollow cathode geometry as used in the AES case. Expected benefits include more efficient particle vaporization, confinement in the ionization volume, and overall ionization. More effective mass spectrometry duty cycle and sensitivity could also be envisioned through the use of ion trap or time-of-flight mass analyzers. The use of negative ion monitoring for enhanced detection of heteroatom-containing organics also holds promise.

Figure 23:
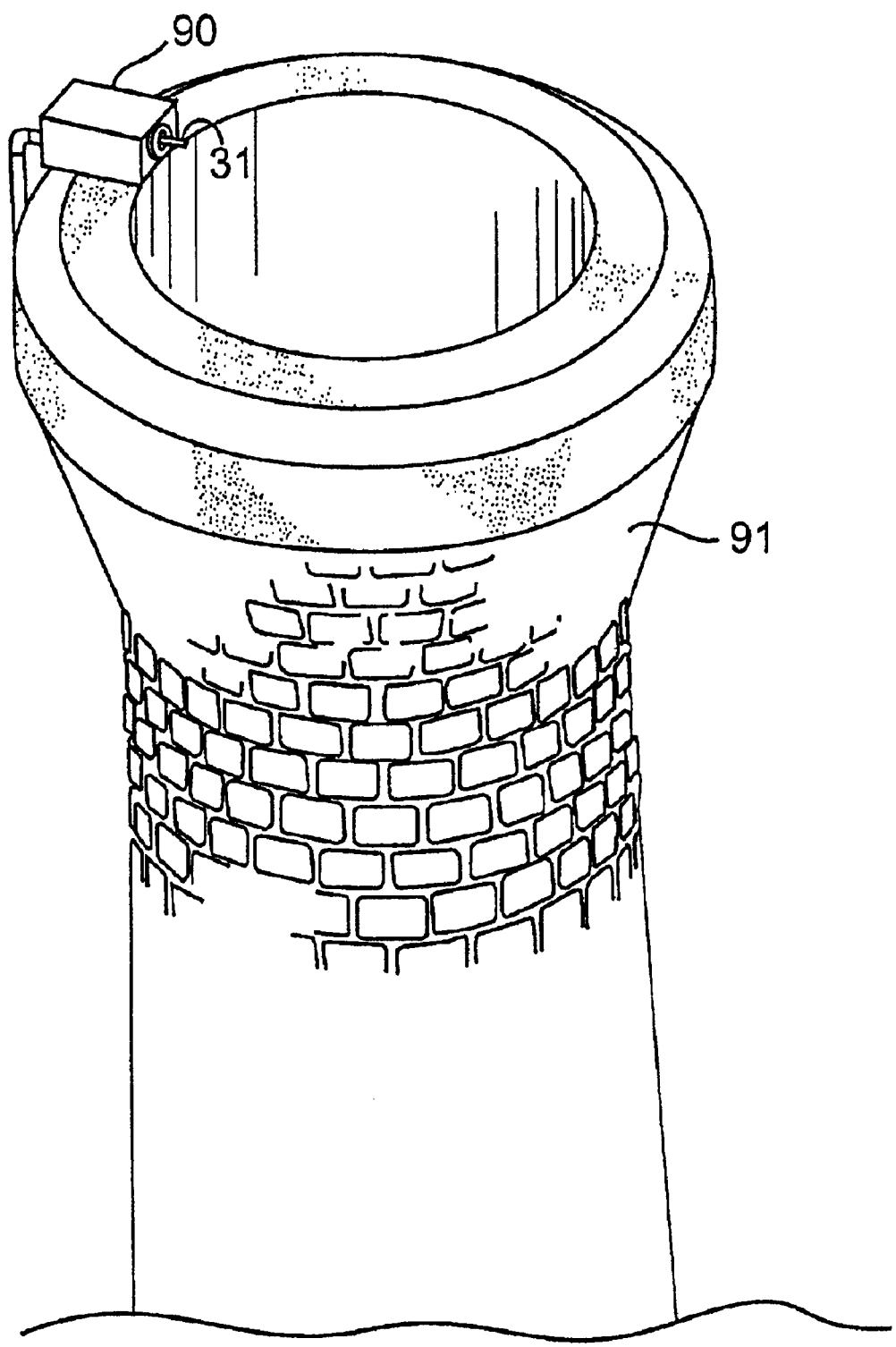
FIG. 23 shows an elevated perspective view of an embodiment of the PB-GD system of the present invention disposed to operate in a remote location.

At this early stage of development, more rigorous characterization and improvements remain, though it is believed that the particle beam-glow discharge approach possesses many of the traits that can be envisioned for future batch-type (either collected or airborne) particle analysis systems. Such instrumentation will likely need to produce both particle size and comprehensive (elemental and molecular) chemical composition information, as is already provided in single-particle analysis systems. It is not difficult to imagine that a relatively simple light scattering arrangement 70, 71 could be placed in the particle flight path of the PB-GD systems of the present invention to provide particle size information. Operation in the laboratory setting and operation in a remote location will also be desirable. An example of the latter is shown in FIG. 23, in which an embodiment 90 of the PB-GD system of the present invention is disposed at the discharge opening of a smokestack 91 spewing airborne particulates. Finally, the use of such a system as a means to assess particle production in plasma deposition/reaction systems or atmospheric modeling chambers would also be a possible application.

1. *Fed. Regist.* 1997, 62, 38651–38752.
2. Henry, C. *Anal. Chem.* 1998, 70, 462–465A.
3. Jambers, W.; De Bock, L.; Van Grieken, R. *Analyst,* 1995, 120, 681–692.
4. Radziemski, L. J.; Loree, T. R.; Cremers, D. A.; Hoffman, N. M. *Anal. Chem.* 1983, 55, 1246–1252.
5. Hahn, D. W. *Appl. Phys. Lett.* 1998, 72, 2960–2962.
6. Neuhauser, R. E.; Panne, U.; Niessmer, R.; Petrucci, G. A.; Cavalli, P.; Omenetto, N. *Anal. Chim. Acta* 1997, 346, 37–48.
7. Johnston, M. V.; Wexler, A. S. *Anal. Chem.* 1995, 67, 721–726A.
8. Prather, K. A.; Nordmeyer, T.; Salt, K. *Anal. Chem.* 1994, 66, 1403–1407.
9. Salt, K.; Noble, C. A.; Prather, K. A. *Anal. Chem.* 1996, 68, 230–234.
10. Noble, C. A.; Prather, K. A. *Environ. Sci. Technol.* 1996, 30, 2667–2680.
11. Morrical, B. D.; Fergenson, D. P.; Prather, K. A. *J. Am. Soc. Mass Spectrom.* 1998, 9, 1068–1073.
12. Carson, P. G.; Neubauer, K. R.; Johnston, M. V.; Wexler, A. S. *J. Aerosol Sci.* 1995, 26, 535–545.
13. Neubauer, K. R.; Johnston, M. V.; Wexler, A. S. *Int. J. Mass Spectrom. Ion Process.* 1997, 163, 29–37.
14. Ge, Z.; Wexler, A. S.; Johnston, M. V. *Environ. Sci. Technol.* 1998, 32, 3218–3223.
15. Yang, M.; Dale, J. M.; Whitten, W. B.; Ramsey, J. M. *Anal. Chem.* 1995, 67, 1021–1025.
16. Reilley, P. T. A.; Gieray, R. A.; Yang, M.; Whitten, W. B.; Ramsey, J. M. *Anal. Chem.* 1997, 69, 36–39.
17. Aardahl, C. L.; Widmann, J. F.; Davis, E. J. *Appl. Spectrosc.* 1998, 52, 47–53.
18. Claes, M.; Gysels, K.; Van Grieken, R. *Inorganic Composition of Atmospheric Aerosols*. In Atmospheric Particles; Harrison, R. M.; Van Grieken, R. E. Eds.; Wiley: Chichester, 1998: Chapter 3.
19. Wang, C.-F.; Miau, T. T.; Perng, J. Y.; Yeh, S. J.; Chiang, P. C.; Tsai, H. T.; Yang, M. H. *Analyst* 1989, 114, 1067–1070.
20. Jalkanen, L. M.; Häsänen, E. K. *J. Anal. At Spectrom.* 1996, 11, 365–369.
21. Tanaka, S.; Yasushi, N.; Sto, N.; Fudasawa, T.; Santosa, S. J.; Yamanaka, K.; Ootoshi, T. *J. Anal. At Spectrom.* 1998, 13, 135–140.
22. Alexander, M. L.; Smith, M. R.; Hartman, J. S.; Mendoza, A.; Koppenaal, D. W. *Appl. Surf. Sci.* 1998, 127, 255–261.
23. Ludke, C.; Hoffmann, E.; Skole, J. Fresenius *J. Anal. Chem.* 1994, 350, 272–276.
24. Bitterli, B. A.; Cousin, H.; Magyar, B. *J. Anal. At. Spectrom.* 1997, 12, 957–961.
25. Takara, H.; Iwasaki, M.; Tanibata, Y. *IEEE Trans. Instr. Measur.* 1995, 44, 819–823.
26. Skelly-Frame, E. M.; Takamatsu, Y.; Suzuki, T. *Spectroscopy* 1996, January, 17–22.
27. Schelles, W.; Maes, K. J. R.; De Gendt, S.; Van Grieken, R. *Anal. Chem.* 1996, 68, 1136–1142.
28. U.S. Patent Pending.
29. You, J.; Fanning, J. C.; Marcus, R. K. *Anal. Chem.* 1994, 66, 3916–3924.
30. You, J.; De Palma, P. A., Jr.; Marcus, R. K. *J. Anal. At. Spectrom.* 1996, 11, 483–490.
31. You, J.; Dempster, M. A.; Marcus, R. K. *Anal. Chem.* 1997, 69, 3419–3426.

32. You, J.; Dempster, M. A.; Marcus, R. K. *J. Anal. At Spectrom.* 1997, 12, 807–815.
33. Duckworth, D. C.; Marcus, R. K. *J. Anal. At. Spectrom.* 1992, 7, 711–715.
34. McLuckey, S. A.; Glish, G. L.; Asano, K. G.; Grant, B. C. *Anal. Chem.* 1988, 60, 2220–2227.
35. Fang, D.; Marcus, R. K. *Fundamental Plasma Processes.* In Glow Discharge Spectroscopies; Marcus, R. K. Ed.; Plenum: N.Y., 1993; Chapter 2.
36. Caroli, S; Senofonte, O. *Hollow Cathode Discharges.* In Glow Discharge Spectroscopies; Marcus, R. K. Ed.; Plenum: N.Y., 1993; Chapter 6.

While a preferred embodiment of the invention has been described using specific terms, such description is for illustrative purposes only, and it is to be understood that changes and variations may be made without departing from the spirit or scope of the following claims.

What is claimed is:

1. An apparatus for sampling and preparing gaseous matter with entrained particulate matter for analysis, the apparatus comprising:
    a device for producing a low pressure plasma, said device having a particle input port configured and disposed for receiving particles to be analyzed;
    a momentum separator having a particle exit port configured for releasing a beam of particles and connected in communication with said particle input port of said device, said momentum separator having a particle entrance port connected in communication with said particle exit port; and
    a conduit having an exit opening connected in communication with said particle entrance port of said momentum separator, said conduit having an entrance opening connected in communication with said exit opening and configured and disposed to receive particles to be analyzed, said conduit being configured to transport therethrough the particles from said entrance opening to said exit opening and wherein said conduit includes a restrictive flow portion having an effective flow diameter in the range of about 0.5 to 4.0 millimeters and disposed between said entrance opening and said entrance port of said momentum separator.

2. An apparatus as in claim 1, wherein said device for producing a low pressure plasma is a glow discharge unit.

3. An apparatus as in claim 1, wherein said device for producing a low pressure plasma is configured and disposed for receiving particles to be analyzed in a sampling region at a first pressure in the range of 0.1 torr to 10.5 torr.

4. An apparatus for sampling and preparing gaseous matter with entrained particles for analysis, the apparatus comprising:
    a momentum separator having a particle entrance port configured for receiving an input of gaseous matter with entrained particles, said momentum separator being configured for removing the particles from the input of gaseous matter with entrained particles, said momentum separator having a particle exit port connected in communication with said particle entrance port and configured for releasing a beam of particles, said momentum separator being configured and disposed for removing at least one gaseous component from the input;
    a conduit having an exit opening connected in communication with said particle entrance port of said momentum separator, said conduit having an entrance opening connected in communication with said exit opening and configured and disposed to receive an input of gaseous matter with entrained particles and transport the input from said entrance opening to said exit opening; and
    an instrument configured and disposed for analyzing said at least one gaseous component.

5. An apparatus as in claim 4, wherein said instrument includes a glow discharge unit.

6. An apparatus for sampling and preparing gaseous matter with entrained particulate matter for analysis, the apparatus comprising:
    a glow discharge unit having a particle input port configured and disposed for receiving particles to be analyzed and providing energy that ionizes and excites the particles in a sampling region;
    a momentum separator having a particle exit port configured for releasing a beam of particles and connected in communication with said particle input port of said glow discharge unit, said momentum separator having a particle entrance port connected in communication with said particle exit port;
    a first instrument configured and disposed for analyzing the atomic emission from said sampling region of said glow discharge unit; and
    a second instrument configured and disposed for mass spectrometric analysis of particles from said sampling region of said glow discharge unit.

7. An apparatus as in claim 6, wherein said first and second instruments are configured and disposed for performing simultaneously on the particles from said sampling region of said glow discharge unit, atomic emission analysis and mass spectrometric analysis.

8. An apparatus as in claim 6, further comprising:
    a third instrument configured and disposed to obtain information about the size distribution of the particles in the particle beam, said third instrument being disposed to operate on the particle beam before the particle beam enters into the glow discharge unit.

9. An apparatus as in claim 8, wherein said third instrument comprises a low-power laser scattering device.

10. An apparatus as in claim 6, wherein said momentum separator includes a chamber connected to a pump, and the apparatus further comprises at least a third instrument and an auxiliary bleed line, said auxiliary bleed line being connected in communication with said pump, said third instrument being configured and disposed for analyzing the gases drawn into said auxiliary bleed line.

11. An apparatus as in claim 10, wherein said third instrument includes a second glow discharge unit.

12. An apparatus as in claim 10, wherein said third instrument is configured and disposed for analyzing the atomic emission from the gases drawn into said auxiliary bleed line.

13. An apparatus as in claim 10, wherein said third instrument is configured and disposed for performing mass spectrometric analysis of the gases drawn into said auxiliary bleed line.

14. A method for sampling and preparing gaseous matter with entrained particulate matter for analysis, the method comprising:
    using a conduit to generate and transport a stream including particulate matter to the entrance port of a momentum separator wherein said conduit has an entrance opening and a restricted flow portion having an effective flow diameter in the range of about 0.5 to 4.0 millimeters and disposed between said entrance opening and said entrance port of said momentum separator;

using said momentum separator to provide a beam containing particulate matter to be analyzed;

providing particulate matter in the beam into a device for producing a low pressure plasma; and using said device to provide energy that ionizes and excites the particulate matter in a sampling region so that the particulate matter can be analyzed.

15. A method as in claim 14, further comprising the step of using at least one of atomic emission and mass spectrometry to analyze the ionized and excited particulate matter.

16. A method as in claim 15, wherein before said analyzing step, the ionized and excited particulate matter is collected in situ in said sampling region until a sufficient amount of the ionized and excited particulate matter is available for performing said analyzing step.

17. A method as in claim 14, further comprising the step of analyzing the ionized and excited particulate matter by simultaneously performing atomic emission analysis and mass spectrometry analysis on the ionized and excited particulate matter.

18. A method as in claim 17, wherein before said analyzing step, the ionized and excited particulate matter is collected in situ in said sampling region until a sufficient amount of the ionized and excited particulate matter is available for performing said analyzing step.

19. A method as in claim 14, further comprising the step of:

before providing the particulate matter in the beam into said glow discharge unit, subjecting the particulate matter to particle sizing analysis.

20. A method as in claim 19, wherein said analysis of ionized and excited particulate matter is effected using at least one of atomic emission and mass spectrometry.

21. A method as in claim 19, wherein said sizing analysis is effected using low-power laser scattering.

22. A method as in claim 14, wherein said stream including particulate matter also includes at least one said gaseous component and the method includes the further step of using one of atomic emission analysis and mass spectrometry analysis on said at least one gaseous component.

23. A method as in claim 15, wherein before using said conduit the particulate matter is collected ex situ and delivered to the entrance opening of said conduit.

24. A method as in claim 17, wherein before using said conduit, the particulate matter is collected ex situ and delivered to the entrance opening of said conduit.

* * * * *